US006222024B1

(12) United States Patent
Goff et al.

(10) Patent No.: US 6,222,024 B1
(45) Date of Patent: Apr. 24, 2001

(54) NUCLEIC ACIDS ENCODING A HUMAN IMMUNODEFICIENCY VIRUS TYPE 1 (HIV-1) INTEGRASE INTERACTOR PROTEIN (INI-1)

(75) Inventors: Stephen P. Goff, Tenafly, NJ (US); Ganjam V. Kalpana, Yonkers, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 08/248,355

(22) Filed: May 24, 1994

(51) Int. Cl.[7] .......................... C07H 21/02; C07H 21/04; A01N 63/00; A61K 48/00
(52) U.S. Cl. ...................... 536/23.1; 424/93.2; 430/350; 435/172.3
(58) Field of Search .................... 435/69.1, 70.1, 435/172.3; 536/23.1; 430/350, 188.1

(56) References Cited

U.S. PATENT DOCUMENTS 5,283,173  2/1994  Fields et al. ............................. 435/6

OTHER PUBLICATIONS

Yu and Haggard–Ljungquist, 1993 J. Bacteriol. 175:1239–1249.*
Yu and Haggard–Ljungquist, 1993 J. Bacteriol. 175:7848–7855.*
Segall et al., 1994 EMBO J. 13:4536–4548.*
Nash et al., 1987 J. Bacteriol. 169:4124–4127.*
Abrams, E. et al. (1986) "Molecular analysis of SNF2 and SNF5, genes required for expression of glucose–repressible genes in S. cervisae" Mol. Cell. Biol. 6: 3643–3651 (Exhibit C).
Chalker, D.L., and Sandmeyer, S.B. (1990) "Transfer RNA genes are genomic targets for de novo transposition of the yeast retrotransposon Ty3", Genetics 126: 837–850 (Exhibit D).
Chalker, D.L. and Sandmeyer, S. B., (1992) "Ty3 integrates within the region of RNA polymerase III transcription initiation" Genes Dev.6: 117–128 (Exhibit E).
Fields, S., and Song, O.K., (1989) "A novel genetic system to detect protein–protein interactions," Nature 340 : 245–246 (Exhibit F) Ji, H., et al., (1993) "Hotspots for unselected Ty1 transposition events on yeast chromosome III are near tRNA genes and LTR sequences" Cell 73: 1007–1018 (Exhibit G).
Ji, H., et al., (1993) "Hotspots for unselected Ty1 transposition events on yeast chromosome III are near tRNA genes and LTR sequences" Cell 73: 1007;1018 (Exhibit G).
Kalpana, G.V., and Goff, S.P. (1993) "Genetic analysis of homomeric interactions of human immunodeficiency virus type 1 integrase using the yeast two–hybrid system" Proc. Natl. Acad. Sci. USA 90: 10593–10597 (Exhibit H).

Laurent, B., and Carlson, M. (1992) "Yeast SNF2/SWI2, SNF5, and SNF6 proteins function coordinately with the gene–specific transcriptional activators GAL4 and Bicoid" Genes Dev. 6: 1707–1715 (Exhibit I).

Laurent, B.C., et al., (1990) "The SNF5 protein of saccharomyces cerevisiae is a glutomine and proline–rich transcriptional activator that affects expression of a broad spectrum of genes" Mol. Cell. Biol. 10: 5616–5625 (Exhibit J).

Laurent, B.C., et al., (1991) "Functional interdependence of the yeast SNF2, SNF5, and SNF6 proteins in transcriptional activation" Proc. Natl. Acad. Sci. USA 88: 2687–2691 (Exhibit K).

Luban, J. et al., (1992) "Genetic assay for multimerization of retroviral gag polyproteins" J. Virol. 66: 5157–5160 (Exhibit L).

Luban, J. et al., (1993) "Human immunodeficiency virus type 1 Gag protein binds to cyclophilins A and B" Cell 73: 1067–1078 (Exhibit M).

Natsoulis, G. et al., (1989) "Ty1 transposition in Saccharomyces cerevisiae is nonrandom" Genetics 123 : 269–279 (Exhibit N).

(List continued on next page.)

Primary Examiner—Donald E. Adams
Assistant Examiner—Jeffrey S. Parkin
(74) Attorney, Agent, or Firm—John P. White; Cooper & Dunham LLP

(57) ABSTRACT

Upon entry into a host cell, retroviruses direct the reverse transcription of the viral RNA genome and the establishment of an integrated proviral DNA. The retroviral integrase protein (IN) is responsible for the insertion of the viral DNA into host chromosomal targets. The IN catalyzes two specific biochemical reactions: (i) cleavage of the 3'termini of the viral DNA to produce 3'-OH ends, and (ii) joining of the two newly generated 3'-termini to the 5'-phosphates on each strand of the target sequence in a concerted strand-transfer reaction. The yeast two-hybrid system was used to identify a novel human gene product, herein designated integrase interactor 1 or INI-1, that binds tightly to the human immunodeficiency virus type 1 (HIV-1) integrase in vitro. Approximately $10^6$ complementary DNAs (cDNAs) of the HL60 macrophage-monocytic cell line were expressed as GAL4AC (activation domain) fusions and tested for coactivation of a reporter gene together with a GAL4DB (DNA binding) IN fusion. Overlapping cDNA clones were identified and their nucleotide sequences ascertained. Nucleotide sequence analysis revealed that INI-1 displays limited amino acid homology to the yeast SNF5 protein, a transcriptional activator required for high-level expression of many disparate cellular genes. Nucleotide sequences encoding the INI-1 gene product will prove useful for the generation of biochemical reagents and the development novel HIV-1 antiviral agents.

15 Claims, 10 Drawing Sheets

OTHER PUBLICATIONS

Neigheborn, L., and Carlson, M. (1984) "Genes affecting the regulation of SUC2 gene expression by glucose repression in saccharomyces cerevisiae" Genetics 108 : 845–858 (Exhibit O).

Peterson, D.C., and Herskowitz, I. (1992) "Characterization of the yeast SWI1, SWI2, SWI3 genes which encode a global activator of transcription" Cell 68 : 573–583 (Exhibit P).

Pryciak, P.M. et al., (1992) "Retroviral integration into minichro–mosomes in vitro" EMBO J. 11 : 291–303 (Exhibit Q).

Sandmeyer, S.B. et al., (1990) "Integration specificity of retrotransposons and retroviruses" Ann. Rev. Genet. 24 : 491–518 (Exhibit R).

Yoshinaga, S.K. et al., (1992) "Roles of SWI1, SWI2, and SWI3, proteins for transcriptional enhancement by steroid receptors" Science 258 : 1598–1604 (Exhibit S).

* cited by examiner

FIG. 4A

SEQ. I.D. NO.: 1-2

```
 -69  GCC CCG GCC CCG CCC CAG CCC TCC CTC GCA GCC CGG CTC
 -24  CGG CCG CCC GCC TCT GCC GCC GTG TCC ATG ATG GCG CTG AGC          7
                                          M   M   A   L   S
  22  AAG ACC TTC GGG CAG AAG CCC GGC ATC TTC CAG CTG GAC GAC         22
      K   T   F   G   Q   K   P   G   I   F   Q   L   D   D
  67  GGC GAG TTC TAC ATG TCT GTG TAC AAG TCC GAG TAC CTC CGT         37
      G   E   F   Y   M   S   V   Y   K   S   E   Y   L   R
 112  ATG TTC CGA GGT ACT GTG GAA AGA AGG AGG TCA TGG AGG             52
      M   F   R   G   T   V   E   R   R   R   S   W   R
 157  CGA CTA GCC AAA ACA CCT AAC CTG ACC ATA GTT GCA TCG TCA         67
      R   L   A   K   T   P   N   L   T   I   V   A   S   S
 202  CAT GGT AAA GCC AGT GTG ACC TTA AAG TAC AAG GAT CAC TAC ACG     82
      H   G   K   A   S   V   T   L   K   Y   K   D   H   Y   T
 247  ACT CTA GCC ACC AGT GGC AAC GAT GAG GAA TAC GCT CAC GGA GTG GAA 97
      T   L   A   T   S   G   N   D   E   E   Y   A   H   G   V   E
 292  GAG ATT CTG GAT CCC CCC TAC ATC AGG TCC AAC TAC AAG AGC GTG TCC ATC  112
      E   I   L   D   P   P   Y   I   R   S   N   Y   K   S   V   S   I
 337  AGC ACA GAG CCC CCT GTA CTG ACC CTG TCC AGG TCC AAC AGG AAG AGG    127
      S   T   E   P   P   V   L   T   L   S   R   S   N   R   K   R
 382  AAC AGC CAG TGG CCA TGC TCC ACC TTC CCC TTT CAG AGG TCC AAC CAC CAC TTA  142
      N   S   Q   W   P   C   S   T   F   P   F   Q   R   S   N   H   H   L
 427  GAT GCC GTG AAG AGA AGA ACC GAG TTC CCC CTT TGC CAG CCC ATG CGC ATG GGC  157
      D   A   V   K   R   R   T   E   F   P   L   C   Q   P   M   R   M   G
 472  CGA GAC AAG AAG CGT CAT CAT CTT TCT GCA AAC AAC TGC TTT GAT GAC CAT GAC  172
      R   D   K   K   R   H   H   L   S   A   N   N   C   F   D   D   H   D
 517  CCA GCT GTG ATC GAT GAG ATG TCT CAG CAG GGG CAG GAG AAG CTG GTC          187
      P   A   V   I   D   E   M   S   Q   Q   G   Q   E   K   L   V
 562  CCC ATC CGG CTG GAC ATG GAG ATC GAT GAT GAG ATG CGA GAC                  202
      P   I   R   L   D   M   E   I   D   D   E   M   R   D
```

FIG. 4B

| | | | | | | | | | | |
|---|---|---|---|---|---|---|---|---|---|---|
| 607 | GCC<br>A | TTC<br>F | ACC<br>T | TGG<br>W | AAC<br>N | ATG<br>M | AAT<br>N | GAG<br>E | AAG<br>K | TTG<br>L | ATG<br>M | ACG<br>T | CCT<br>P | GAG<br>E | ATG<br>M | 217 |
| 652 | TTT<br>F | TCA<br>S | GAA<br>E | ATC<br>I | CTC<br>L | TGT<br>C | GAC<br>D | GAT<br>D | CTG<br>L | GAT<br>D | TTG<br>L | AAC<br>N | CCG<br>P | CTG<br>L | ACG<br>T | 232 |
| 697 | TTT<br>F | GTG<br>V | CCA<br>P | ATC<br>I | GCC<br>A | ATC<br>I | TCT<br>S | GCC<br>A | ATC<br>I | AGA<br>R | CAG<br>Q | CAG<br>Q | ATC<br>I | GAG<br>E | TCC<br>S | 247 |
| 742 | TAC<br>Y | CCC<br>P | ACG<br>T | GAC<br>D | AGC<br>S | GAC<br>D | CTG<br>L | GAG<br>E | ATC<br>I | TCA<br>S | CAG<br>Q | GAC<br>D | CAG<br>Q | CGC<br>R | GTC<br>V | 262 |
| 787 | ATC<br>I | ATC<br>I | AAG<br>K | CTG<br>L | AAC<br>N | ATC<br>I | CAT<br>H | GTG<br>V | GGA<br>G | ATT<br>I | TCC<br>S | CTG<br>L | GTG<br>V | GAC<br>D | AAG<br>K | 277 |
| 832 | CAG<br>Q | TTT<br>F | GAG<br>E | TGG<br>W | GAC<br>D | ATG<br>M | TCA<br>S | AAC<br>N | GAG<br>E | (AAC)<br>N | GAG<br>E | TCA<br>S | GGG<br>G | GAG<br>E | TTT<br>F | 292 |
| 877 | TTT<br>F | GCC<br>A | CTG<br>L | TGC<br>C | CTG<br>L | TCG<br>S | AGC<br>S | GAG<br>E | CTG<br>L | TTG<br>L | GGC<br>G | CTG<br>L | GAG<br>E | GAG<br>E | TTT<br>F | 307 |
| 922 | GTC<br>V | ACC<br>T | ACT<br>T | ATC<br>I | TAC<br>Y | TTC<br>F | AGC<br>S | ATC<br>I | CGG<br>R | CAG<br>Q | CTG<br>L | CCC<br>P | AGC<br>S | TGG<br>W | CAT<br>H | 322 |
| 967 | CAG<br>Q | AAG<br>K | TAC<br>Y | ATC<br>I | GCA<br>A | TAC<br>Y | TTC<br>F | AGC<br>S | GGC<br>G | AAC<br>N | CCT<br>P | CCC<br>P | ACA<br>T | GTG<br>V | GAG<br>E | 337 |
| 1012 | ATT<br>I | GCC<br>A | ATC<br>I | CGG<br>R | AAC<br>N | ACG<br>T | AGG<br>R | ATC<br>I | GAG<br>E | GAG<br>E | GCG<br>A | ATG<br>M | GAG<br>E | AAG<br>K | TGC<br>C | CCA<br>P | CTG<br>L | 352 |
| 1057 | CTG<br>L | GAG<br>E | ACT<br>T | CTG<br>L | ACA<br>T | GAC<br>D | GCT<br>A | GAG<br>E | ATG<br>M | GAG<br>E | AAG<br>K | CTT<br>L | CTT<br>L | CGC<br>R | GAC<br>D | 367 |
| 1102 | CAG<br>Q | GAC<br>D | AGG<br>R | AAC<br>N | ACG<br>T | AGG<br>R | CGT<br>R | ATG<br>M | AGG<br>R | CGG<br>R | CAG<br>Q | GCC<br>A | AAC<br>N | ACG<br>T | GAG<br>E | 382 |
| 1147 | CCG<br>P | GCC<br>A | TGG<br>W | TAA<br>*** | CCA | GCC | CAT | CAC | ACG | GCT | ACG | CCC | ACG | GAG | CAT | 385 |

FIG. 4C

```
1192  CTC AGA AGA TTG GGC CGC CTC TCC TCC ATC TTC TGG CAA GGA CAG
1237  AGG CGA GGG GAC AGC CCA AGG TGG CCA TCC TGA CCG GGT GGG GGT
1282  GGA GTG GGG GCT TCC TCC GCG TGG CCC TTC GTA CAC ATT CCA TTT
1327  GTT GAG CCC CAG TCC TCC AGG TGC CCA CCC TAC CCC TCC
1372  CCA GTC TCT GGG GTC AGC CCC AAA CCT TAT AGG TTG TGT TTT
1417  GTT TTG TAT AGG CCC ATG CAG TAG GGC TAA CAG TTA AAT
1462  AAA AGG CAA CAG GTC TTC AAAAAAAAAA
      AAT TTC TTA AAT CTA GTG TCT TTA
1507  TTT CTT CTG TTA CAA TAG TGT TTG TGT AAG CAG GTT AGA GTG
1552  CAC AGT GTC CCC AAT AAT TGT TCC CAC AAT ACC AAA TTA AAC
1597  AAT CCC ACA AAG AAT TCT GAC ATC AAT GTG TTT TCC TCA GTC AGG
1642  TCT ATT TCA AGA TTC TAG AAG TTC CTT TTG TAA AAC TTG CCT TTA
1687  AAA CTC TTC CTC CTA ATG CCA TCA GAT CTC TTA ACA TTG GCT CAC
1732  TGT GGG ATC TTT CTT AGG TTG AAT TTC AAT GTG TAC ATC AAA
1777  GTG CCT TTT TC 1787
```

FIG. 5B

SEQ. I.D. NO.: 3-4

```
ini-1  180  ..ASQPEVLVPIRLDMEIDGQK..LRDAFTWNMNEKLMTPEMFSEILCDDLD
SNF5   451  ..NETSEQLVPIRLEFDQDRDRFFLRDTLLWNKDKLIKIEDFVDDMLRDYR
                                     <----------region I---------->

228  LNPLI...FVPAIASAIRQQIESYPTDSILE......DQSDQRVIKLNI
       501  FEDATREQHIDTICQSIQEQIQEFQGNPYIELNQDRLGGDDLRIRKLDI
                                                    <----------

269  HVGNISLVDQFEWDMSEKENSPEKFALKLCSELGLGGEFVTTIAYSIRGQ
       551  VVGQNQLIDQFEWDISNSDNCPEEFAESMQQELELPGEFVTAIAHSIREQ
                                     ---region II---------->

319  LSWHQKTYAFSEN...........PLPTVEIAIRNTGDADQWCP
       601  VHMYHKSLALLGYNFDGSAIEDDDIRSRMLPTIILDDVYRPAAESKIFTP

352  LIETLTDAEMEKKIRDQDRNTRRMRRLANTAP...  383
       651  NILQISAAELERLDKDKDRDTRRKRRQGRSNR..   682
            <----------region III---------->
```

Coomassie stained PAGE

Western with IN Ab

FIG. 7A
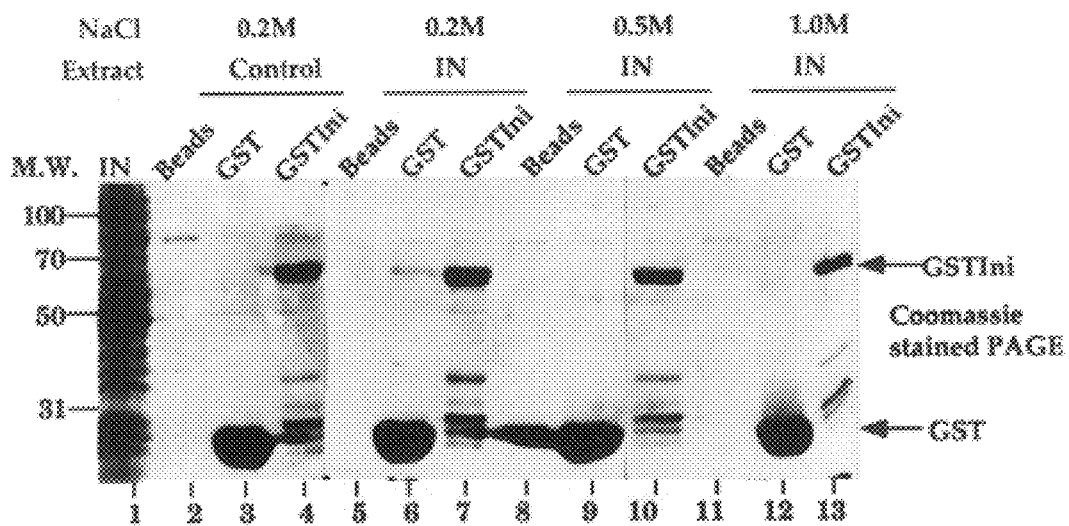
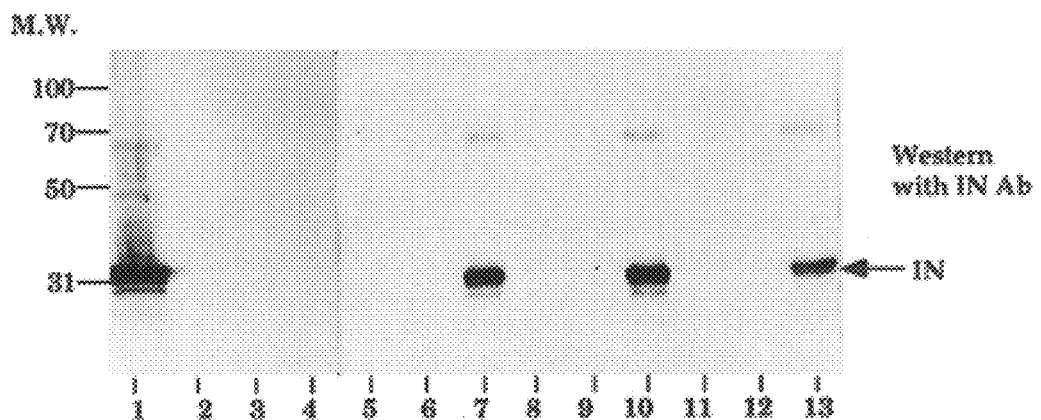
FIG. 7B

SEQUENCE LISTING

```
(1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 1867 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: N (iv) ANTI-SENSE: N (v) FRAGMENT TYPE: N-terminal (ix) FEATURE:
       (A) NAME/KEY: CDS
       (B) LOCATION: 70..1225
       (D) OTHER INFORMATION:

(xi) SEQUENCE DESCRIPTION: SEQ ID NO:1:

GCCCCGGCCC CGCCCCAGCC CTCCTGATCC CTCGCAGCCC GGCTCCGGCC GCCCGCCTCT         60

GCCGCCGCA ATG ATG ATG ATG GCG CTG AGC AAG ACC TTC GGG CAG AAG          108
           Met Met Met Met Ala Leu Ser Lys Thr Phe Gly Gln Lys
             1               5                  10

CCC GTG AAG TTC CAG CTG GAG GAC GAC GGC GAG TTC TAC ATG ATC GGC         156
Pro Val Lys Phe Gln Leu Glu Asp Asp Gly Glu Phe Tyr Met Ile Gly
         15                  20                  25

TCC GAG GTG GGA AAC TAC CTC CGT ATG TTC CGA GGT TCT CTG TAC AAG         204
Ser Glu Val Gly Asn Tyr Leu Arg Met Phe Arg Gly Ser Leu Tyr Lys
 30                  35                  40                  45

AGA TAC CCC TCA CTC TGG AGG CGA CTA GCC ACT GTG GAA GAG AGG AAG         252
Arg Tyr Pro Ser Leu Trp Arg Arg Leu Ala Thr Val Glu Glu Arg Lys
                 50                  55                  60

AAA ATA GTT GCA TCG TCA CAT GGT AAA AAA ACA AAA CCT AAC ACT AAG         300
Lys Ile Val Ala Ser Ser His Gly Lys Lys Thr Lys Pro Asn Thr Lys
             65                  70                  75

GAT CAC GGA TAC ACG ACT CTA GCC ACC AGT GTG ACC CTG TTA AAA GCC         348
Asp His Gly Tyr Thr Thr Leu Ala Thr Ser Val Thr Leu Leu Lys Ala
         80                  85                  90

TCG GAA GTG GAA GAG ATT CTG GAT GGC AAC GAT GAG AAG TAC AAG GCT         396
Ser Glu Val Glu Glu Ile Leu Asp Gly Asn Asp Glu Lys Tyr Lys Ala
 95                 100                 105
```

```
GTG TCC ATC AGC ACA GAG CCC CCC ACC TAC CTC AGG GAA CAG AAG GCC        444
Val Ser Ile Ser Thr Glu Pro Pro Thr Tyr Leu Arg Glu Gln Lys Ala
110             115                 120                 125

AAG AGG AAC AGC CAG TGG GTA CCC ACC CTG TCC AAC AGC TCC CAC CAC        492
Lys Arg Asn Ser Gln Trp Val Pro Thr Leu Ser Asn Ser Ser His His
            130                 135                 140

TTA GAT GCC GTG CCA TGC TCC ACA ACC ATC AAC AGG AAC CGC ATG GGC        540
Leu Asp Ala Val Pro Cys Ser Thr Thr Ile Asn Arg Asn Arg Met Gly
                145                 150                 155

CGA GAC AAG AAG AGA ACC TTC CCC CTT TGC TTT GAT GAC CAT GAC CCA        588
Arg Asp Lys Lys Arg Thr Phe Pro Leu Cys Phe Asp Asp His Asp Pro
            160                 165                 170

GCT GTG ATC CAT GAG AAC GCA TCT CAG CCC GAG GTG CTG GTC CCC ATC        636
Ala Val Ile His Glu Asn Ala Ser Gln Pro Glu Val Leu Val Pro Ile
175                 180                 185

CGG CTG GAC ATG GAG ATC GAT GGG CAG AAG CTG CGA GAC GCC TTC ACC        684
Arg Leu Asp Met Glu Ile Asp Gly Gln Lys Leu Arg Asp Ala Phe Thr
190                 195                 200                 205

TGG AAC ATG AAT GAG AAG TTG ATG ACG CCT GAG ATG TTT TCA GAA ATC        732
Trp Asn Met Asn Glu Lys Leu Met Thr Pro Glu Met Phe Ser Glu Ile
                210                 215                 220

CTC TGT GAC GAT CTG GAT TTG AAC CCG CTG ACG TTT GTG CCA GCC ATC        780
Leu Cys Asp Asp Leu Asp Leu Asn Pro Leu Thr Phe Val Pro Ala Ile
                225                 230                 235

GCC TCT GCC ATC AGA CAG CAG ATC GAG TCC TAC CCC ACG GAC AGC ATC        828
Ala Ser Ala Ile Arg Gln Gln Ile Glu Ser Tyr Pro Thr Asp Ser Ile
            240                 245                 250

CTG GAG GAC CAG TCA GAC CAG CGC GTC ATC ATC AAG CTG AAC ATC CAT        876
Leu Glu Asp Gln Ser Asp Gln Arg Val Ile Ile Lys Leu Asn Ile His
255                 260                 265

GTG GGA AAC ATT TCC CTG GTG GAC CAG TTT GAG TGG GAC ATG TCA GAG        924
Val Gly Asn Ile Ser Leu Val Asp Gln Phe Glu Trp Asp Met Ser Glu
270                 275                 280                 285

AAG GAG AAC TCA CCA GAG AAG TTT GCC CTG AAG CTG TGC TCG GAG CTG        972
Lys Glu Asn Ser Pro Glu Lys Phe Ala Leu Lys Leu Cys Ser Glu Leu
                290                 295                 300

GGG TTG GGC GGG GAG TTT GTC ACC ACC ATC GCA TAC AGC ATC CGG GGA       1020
Gly Leu Gly Gly Glu Phe Val Thr Thr Ile Ala Tyr Ser Ile Arg Gly
            305                 310                 315

CAG CTG AGC TGG CAT CAG AAG ACC TAC GCC TTC AGC GAG AAC CCT CTG       1068
Gln Leu Ser Trp His Gln Lys Thr Tyr Ala Phe Ser Glu Asn Pro Leu
                320                 325                 330

CCC ACA GTG GAG ATT GCC ATC CGG AAC ACG GGC GAT GCG GAC CAG TGG       1116
Pro Thr Val Glu Ile Ala Ile Arg Asn Thr Gly Asp Ala Asp Gln Trp
                335                 340                 345

TGC CCA CTG CTG GAG ACT CTG ACA GAC GCT GAG ATG GAG AAG AAG ATC       1164
Cys Pro Leu Leu Glu Thr Leu Thr Asp Ala Glu Met Glu Lys Lys Ile
350                 355                 360                 365

CGC GAC CAG GAC AGG AAC ACG AGG CGG ATG AGG CGT CTT GCC AAC ACG       1212
Arg Asp Gln Asp Arg Asn Thr Arg Arg Met Arg Arg Leu Ala Asn Thr
                370                 375                 380

GCC CCG GCC TGG T AACCAGCCCA TCAGCACACG GCTCCCACGG AGCATCTCAG         1265
Ala Pro Ala Trp
                385

AAGATTGGGC CGCCTCTCCT CCATCTTCTG GCAAGGACAG AGGCGAGGGG ACAGCCCAGC     1325

GCCATCCTGA GGATCGGGTG GGGGTGGAGT GGGGGCTTCC AGGTGGCCCT TCCCGGTACA     1385

CATTCCATTT GTTGAGCCCC AGTCCTGCCC CCCACCCCAC CCTCCCTACC CCTCCCCAGT    1445
```

-continued

```
CTCTGGGGTC AGGAAGAAAC CTTATTTTAG GTTGTGTTTT GTTTTGTATA GGAGCCCCAG    1505

GCAGGGCTAG TAACAGTTTT TAAATAAAAG GCAACAGGTC ATGTTCAAAA AAAAAAAAAT    1565

TTCTTAAATC TAGTGTCTTT ATTTCTTCTG TTACAATAGT GTTGCTTGTG TAAGCAGGTT    1625

AGAGTGCACA GTGTCCCCAA TTGTTCCTGG CACTGCAAAA CCAAATTAAA CAATCCCACA    1685

AAGAATTCTG ACATCAATGT GTTTTCCTCA GTCAGGTCTA TTTCAAGATT CTAGAAGTTC    1745

CTTTTGTAAA ACTTGCCTTT AAAACTCTTC CTCCTAATGC CATCAGATCT CTTAACATTG    1805

GCTCACTGTG GGATCTTTCC TCTTAGGTTG AATTTCTACG TGAATATCAA AGTGCCTTTT    1865

TC                                                                  1867
```

(2) INFORMATION FOR SEQ ID NO:2:

(i) SEQUENCE CHARACTERISTICS:
        (A) LENGTH: 385 amino acids
        (B) TYPE: amino acid
        (D) TOPOLOGY: linear (ii) MOLECULE TYPE: protein (xi) SEQUENCE DESCRIPTION: SEQ ID NO:2:

```
Met Met Met Met Ala Leu Ser Lys Thr Phe Gly Gln Lys Pro Val Lys
 1               5                  10                  15

Phe Gln Leu Glu Asp Asp Gly Glu Phe Tyr Met Ile Gly Ser Glu Val
                20                  25                  30

Gly Asn Tyr Leu Arg Met Phe Arg Gly Ser Leu Tyr Lys Arg Tyr Pro
            35                  40                  45

Ser Leu Trp Arg Arg Leu Ala Thr Val Glu Glu Arg Lys Lys Ile Val
        50                  55                  60

Ala Ser Ser His Gly Lys Lys Thr Lys Pro Asn Thr Lys Asp His Gly
 65                  70                  75                  80

Tyr Thr Thr Leu Ala Thr Ser Val Thr Leu Lys Ala Ser Glu Val
                 85                  90                  95

Glu Glu Ile Leu Asp Gly Asn Asp Glu Lys Tyr Lys Ala Val Ser Ile
                100                 105                 110

Ser Thr Glu Pro Pro Thr Tyr Leu Arg Glu Gln Lys Ala Lys Arg Asn
            115                 120                 125

Ser Gln Trp Val Pro Thr Leu Ser Asn Ser Ser His His Leu Asp Ala
        130                 135                 140

Val Pro Cys Ser Thr Thr Ile Asn Arg Asn Arg Met Gly Arg Asp Lys
145                 150                 155                 160

Lys Arg Thr Phe Pro Leu Cys Phe Asp Asp His Asp Pro Ala Val Ile
                165                 170                 175

His Glu Asn Ala Ser Gln Pro Glu Val Leu Val Pro Ile Arg Leu Asp
            180                 185                 190

Met Glu Ile Asp Gly Gln Lys Leu Arg Asp Ala Phe Thr Trp Asn Met
        195                 200                 205

Asn Glu Lys Leu Met Thr Pro Glu Met Phe Ser Glu Ile Leu Cys Asp
    210                 215                 220

Asp Leu Asp Leu Asn Pro Leu Thr Phe Val Pro Ala Ile Ala Ser Ala
225                 230                 235                 240

Ile Arg Gln Gln Ile Glu Ser Tyr Pro Thr Asp Ser Ile Leu Glu Asp
                245                 250                 255

Gln Ser Asp Gln Arg Val Ile Ile Lys Leu Asn Ile His Val Gly Asn
            260                 265                 270
```

```
Ile Ser Leu Val Asp Gln Phe Glu Trp Asp Met Ser Glu Lys Glu Asn
    275                 280                 285

Ser Pro Glu Lys Phe Ala Leu Lys Leu Cys Ser Glu Leu Gly Leu Gly
    290                 295                 300

Gly Glu Phe Val Thr Thr Ile Ala Tyr Ser Ile Arg Gly Gln Leu Ser
305                 310                 315                 320

Trp His Gln Lys Thr Tyr Ala Phe Ser Glu Asn Pro Leu Pro Thr Val
                325                 330                 335

Glu Ile Ala Ile Arg Asn Thr Gly Asp Ala Asp Gln Trp Cys Pro Leu
                340                 345                 350

Leu Glu Thr Leu Thr Asp Ala Glu Met Glu Lys Lys Ile Arg Asp Gln
                355                 360                 365

Asp Arg Asn Thr Arg Arg Met Arg Arg Leu Ala Asn Thr Ala Pro Ala
    370                 375                 380

Trp
385

(2) INFORMATION FOR SEQ ID NO:3:

(i) SEQUENCE CHARACTERISTICS:
        (A) LENGTH: 204 amino acids
        (B) TYPE: amino acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (v) FRAGMENT TYPE: N-terminal (xi) SEQUENCE DESCRIPTION: SEQ ID NO:3:

Ala Ser Gln Pro Glu Val Leu Val Pro Ile Arg Leu Asp Met Glu Ile
                  5                  10                  15

Asp Gly Gln Lys Leu Arg Asp Ala Phe Thr Trp Asn Met Asn Glu Lys
                 20                  25                  30

Leu Met Thr Pro Glu Met Phe Ser Glu Ile Leu Cys Asp Asp Leu Asp
                 35                  40                  45

Leu Asn Pro Leu Thr Phe Val Pro Ala Ile Ala Ser Ala Ile Arg Gln
         50                  55                  60

Gln Ile Glu Ser Tyr Pro Thr Asp Ser Ile Leu Glu Asp Gln Ser Asp
65                  70                  75                  80

Gln Arg Val Ile Ile Lys Leu Asn Ile His Val Gly Asn Ile Ser Leu
                 85                  90                  95

Val Asp Gln Phe Glu Trp Asp Met Ser Glu Lys Glu Asn Ser Pro Glu
                100                 105                 110

Lys Phe Ala Leu Lys Leu Cys Ser Glu Leu Gly Leu Gly Gly Glu Phe
            115                 120                 125

Val Thr Thr Ile Ala Tyr Ser Ile Arg Gly Gln Leu Ser Trp His Gln
            130                 135                 140

Lys Thr Tyr Ala Phe Ser Glu Asn Pro Leu Pro Thr Val Glu Ile Ala
145                 150                 155                 160

Ile Arg Asn Thr Gly Asp Ala Asp Gln Trp Cys Pro Leu Leu Glu Thr
                165                 170                 175

Leu Thr Asp Ala Glu Met Glu Lys Lys Ile Arg Asp Gln Asp Arg Asn
            180                 185                 190
```

```
Thr Arg Arg Met Arg Arg Leu Ala Asn Thr Ala Pro
        195                 200
```

(2) INFORMATION FOR SEQ ID NO:4:

(i) SEQUENCE CHARACTERISTICS:
        (A) LENGTH: 232 amino acids
        (B) TYPE: amino acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (v) FRAGMENT TYPE: N-terminal (xi) SEQUENCE DESCRIPTION: SEQ ID NO:4:

```
Asn Glu Thr Ser Glu Gln Leu Val Pro Ile Arg Leu Glu Phe Asp Gln
                 5                  10                  15

Asp Arg Asp Arg Phe Phe Leu Arg Asp Thr Leu Leu Trp Asn Lys Asn
        20                  25                  30

Asp Lys Leu Ile Lys Ile Glu Asp Phe Val Asp Asp Met Leu Arg Asp
        35                  40                  45

Tyr Arg Phe Glu Asp Ala Thr Arg Glu Gln His Ile Asp Thr Ile Cys
    50                  55                  60 ln Ser Ile Gln Glu Gln Ile Gln Glu Phe Gln Gly Asn Pro Tyr Ile
65                  70                  75                  80

Glu Leu Asn Gln Asp Arg Leu Gly Gly Asp Leu Arg Ile Arg Ile
                85                  90                  95

Lys Leu Asp Ile Val Val Gly Gln Asn Gln Leu Ile Asp Gln Phe Glu
            100                 105                 110

Trp Asp Ile Ser Asn Ser Asp Asn Cys Pro Glu Glu Phe Ala Glu Ser
            115                 120                 125

Met Cys Gln Glu Leu Glu Leu Pro Gly Glu Phe Val Thr Ala Ile Ala
    130                 135                 140

His Ser Ile Arg Glu Gln Val His Met Tyr His Lys Ser Leu Ala Leu
145                 150                 155                 160

Leu Gly Tyr Asn Phe Asp Gly Ser Ala Ile Glu Asp Asp Ile Arg
                165                 170                 175

Ser Arg Met Leu Pro Thr Ile Thr Leu Asp Asp Val Tyr Arg Pro Ala
            180                 185                 190

Ala Glu Ser Lys Ile Phe Thr Pro Asn Leu Leu Gln Ile Ser Ala Ala
            195                 200                 205

Glu Leu Glu Arg Leu Asp Lys Asp Lys Asp Arg Asp Thr Arg Arg Lys
    210                 215                 220

Arg Arg Gln Gly Arg Ser Asn Arg
225                 230
```

NUCLEIC ACIDS ENCODING A HUMAN IMMUNODEFICIENCY VIRUS TYPE 1 (HIV-1) INTEGRASE INTERACTOR PROTEIN (INI-1)

The invention disclosed herein was made with Government support under Grant No. AI24845 from the National Institute of Allergy and Infectious Disease. Accordingly, the U.S. Government has certain rights in this invention.

Throughout this application, various references are referred to by author and year in parentheses. Disclosures of these publications in their entireties are hereby incorporated into this application to more fully describe the state of the art to which this invention pertains. Full bibliographic citation for these references may be found at the end of this application, preceding the claims.

BACKGROUND OF THE INVENTION

In the first few hours after entry into a host cell, retroviruses direct the reverse transcription of the RNA genome into DNA, and then the insertion of that DNA into the host genome to form the integrated provirus (Goff, 1992; Weiss et al., 1984). The integration reaction is essential for the successful expression of the viral DNA to give rise to progeny virus, and is responsible for the ability of the virus to persist in the infected cell. The reaction is a highly efficient and orderly process. Specific inverted repeat sequences at the termini of the linear viral DNA, required in cis, are joined to the host DNA. The reaction is associated with specific alterations at the junctions: a small number of base pairs, usually two, are lost from each of the termini of the unintegrated viral DNA, and a small number of base pairs initially present only once at the target site are duplicated so as to flank the integrated provirus.

A single virally encoded enzyme, integrase (IN), is required for the establishment of the integrated provirus. This enzyme is encoded by the 3' portion of the pol gene (Schwartzberg et al., 1984) and is packaged inside the virion particle in the course of virion assembly. During the early stages of infection, the protein remains associated with the viral nucleic acid in a nucleoprotein complex (Farnet and Haseltine, 1991) and performs several specific reactions: first, the 3' termini of the viral DNA are cleaved to produce recessed 3'OH ends, and second, the two newly generated 3' termini are joined to the 5' phosphates on each strand of the target sequence in a concerted strand transfer reaction (Fujiwara and Mizuuchi, 1988). Only one strand of the viral DNA at each terminus is joined to each strand of the target DNA. The positions of attack by each 3' OH end on the two target DNA strands are staggered, such that the initial product contains gaps; host repair enzymes are thought to be responsible for removing unpaired bases, filling in gaps, and ligating the second strand. These repair steps result in the formation of the target site duplication flanking the provirus.

It is possible that some host proteins are directly involved in promoting the integration reactions occurring after viral infection. Although recombinant integrase preparations can carry out all the steps known to be required for processing and joining the viral DNA (Bushman and Craigie, 1991; Bushman et al., 1990; Craigie et al, 1990; Katz et al., 1990), some aspects of the reaction are not fully recapitulated in vitro. For example, the isolated proteins show only very low specific activity for both cutting and joining of DNA (Bushman et al., 1990; Craigie et al., 1990). Furthermore, joining reactions carried out with oligonucleotide substrates for some viruses result in the transfer of only one 3'OH to the target DNA yielding a Y structure, rather than the concerted transfer of two 3'OH termini to the target (Bushman et al., 1990). These inadequacies of the in vitro systems may reflect problems with proper oligomerization of the IN protein, or with the absence of stimulatory cofactors. For some viruses, host proteins might be responsible for stimulation of the overall reaction in vivo, and, especially, for the concerted integration of the two termini at a single locus.

Integration of retroviral DNA occurs on many chromosomes and with no apparent local sequence specificity (Dhar et al., 1980; Hughes et al., 1978; Shimotohno and Temin, 1980; Shoemaker et al., 1981). Several studies, however, suggest that there may be preferred sites for integration. Proviral DNAs established by infection, rather than by transfection with cloned DNAs, seem to be more highly and consistently transcribed, implying that integration sites are selected from transcriptionally active areas of the genome (Hwang and Gilboa, 1984). A significant bias for insertions into open chromatin was detected at high frequency insertion near DNAse hypersensitive sites (Rohdewohld et al., 1987; Vijaya et al., 1986) and into transcriptionally active regions (Scherdin et al., 1990). In addition, there may be a small number of "hot spots", or preferred sites, which are frequently targeted (Shih et al., 1988). Measurements of the frequency of insertional inactivation into particular genes have been shown to give fewer events than predicted, suggesting that there may be "cold spots" as well (King et al., 1985; Varmus et al., 1981). In vitro studies of the integration into SV40 minichromosomes showed that the origin region and linker regions between the nucleosomes tended to exclude insertions, while nucleosomal regions were efficiently targeted; phasing of the insertions in the chromatin could be observed, with a 10-bp periodicity (Pryciak et al., 1991). These results suggest that the presence of DNA binding proteins and histones on DNA can significantly perturb the target choice.

Many of the features of retroviral integration are similar to those associated with transposition of eucaryotic and prokaryotic mobile elements. Analogous studies in various retrotransposon systems also suggest that target sites for integration are non-random. The Ty elements in yeast have been shown to exhibit significant target site biases; Ty1 insertions tend to cluster near the 5' end of some target genes (Natsoulis et al., 1989) and within 400 bp of tRNA genes (Ji et al., 1993), and Ty3 insertions are highly restricted to specific positions relative to polymerase III promoters (Chalker and Sandmeyer, 1990; Chalker and Sandmeyer, 1992). In these cases the integration events are not thought to be affected by the sequence itself or by transcriptional activity, but rather are more likely to be profoundly restricted by host chromosomal proteins, with the potential candidates for the target proteins being the TFIIIB or TFIIIC transcription factors bound to the promoter (Sandmeyer et al., 1990).

The identification of host proteins that might target proviral integration, stimulate integration activity, or affect the incoming retroviral DNA in other ways would provide an important lead into new areas of research. In an attempt to find such proteins, the yeast two hybrid system has been used (Fields et al., U.S. Pat. No. 5,283,173) to screen a cDNA library for proteins that interact with the HIV-1 IN. The search resulted in the recovery of a single novel gene, termed ini-1 for integrase interactor 1 (SEQ ID NO.1). The predicted amino acid sequence (SEQ ID NO.2) of the ini-1 protein shows an unexpected sequence similarity to SNF5, a yeast transcriptional activator required for the high-level expression of many genes (Laurent et al., 1990). The product of the ini-1 gene may serve as an internal receptor for the HIV-1 IN, and may be responsible for targeting integration to active regions of the chromosome.

SUMMARY OF THE INVENTION

This invention provides an isolated nucleic acid encoding an integrase interactor 1 (SEQ ID NO.1) gene (ini-1). The invention further provides a purified polypeptide comprising naturally-occurring ini-1. The invention also provides for the purified polypeptide possesses part or all the amino acid sequence of human ini-1 as shown in FIG. 4 (SEQ ID NO.2) or any naturally occurring allelic variant thereof. The invention further provides methods of determining whether a compound is capable of interfering with the formation of a complex between a retrovirus integrase protein and an ini-1 protein.

Finally, the invention provides for a method of disrupting a retrovirus life cycle in a mammal which comprises administering to the mammal a compound which is capable of disrupting a retrovirus integrase protein-ini-1 protein interaction so as to thereby disrupt the retrovirus life cycle.

Northern analysis of total RNAs from human cell lines hybridized with pD2.1 probe. Lane 1 HeLa; lane 2: CB33; lane 3:Hut78. The amount of RNA loaded in each lane is not equivalent.

Figure 3:
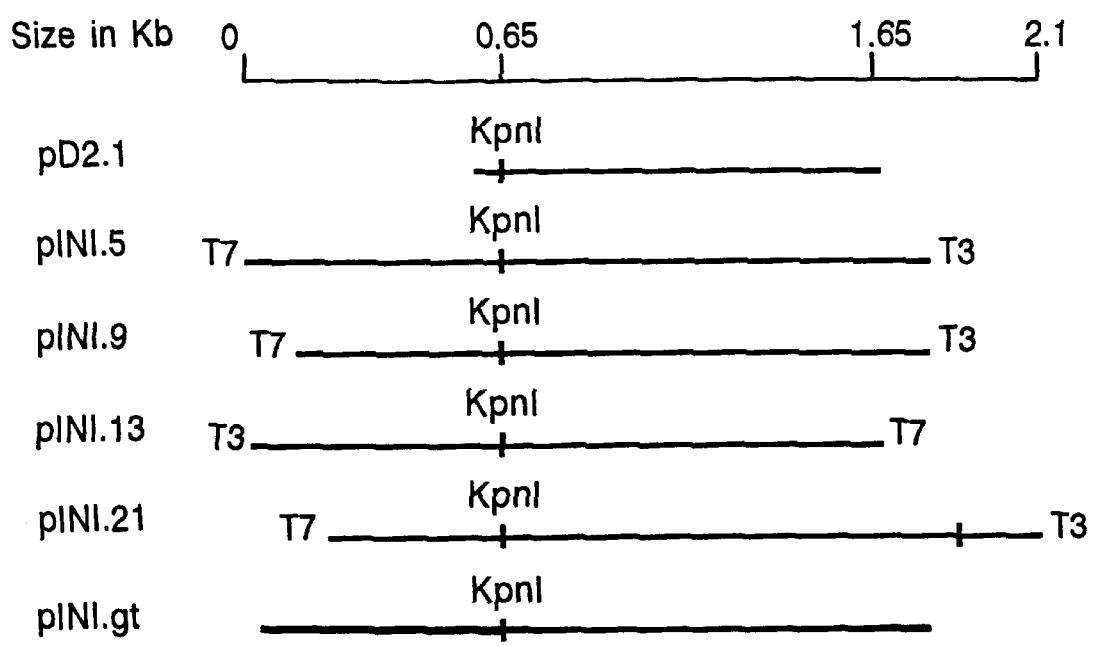

FIG. 3. overlapping CDNA clones encoding ini-1. The top bar (pD2.1) indicates the cDNA insert isolated from the yeast screen. pini-1 to 21 are from a ZAPgt11-HeLa cDNA library and pINI.gt from λgt11-HeLa cDNA library. T7 and T3 indicates the relative position of T7 and T3 promoters with respect to cDNA inserts in the pBluescript vector.

FIG. 4. Sequence of cDNA clone encoding ini-1 (SEQ ID NO:1). Complete sequence deduced from the overlapping ini-1 cDNA clones. The A nucleotide of the first methionine codon was considered nt#1. Amino acid residues are numbered on the right side of the diagram and nucleotides on the left (SEQ ID NO:2). Potential poly(A) addition signal AATAAA is underlined and the start and stop codons are highlighted. The poly(A) stretch in clone pINI.gt is indicated by the stretch of As in the middle of 3' non-coding region. Stop codons are indicated by '***'. The heptad repeat of leucine/valine residues are highlighted. The potential N-linked glycosylation sites are circled.

Figure 5A:
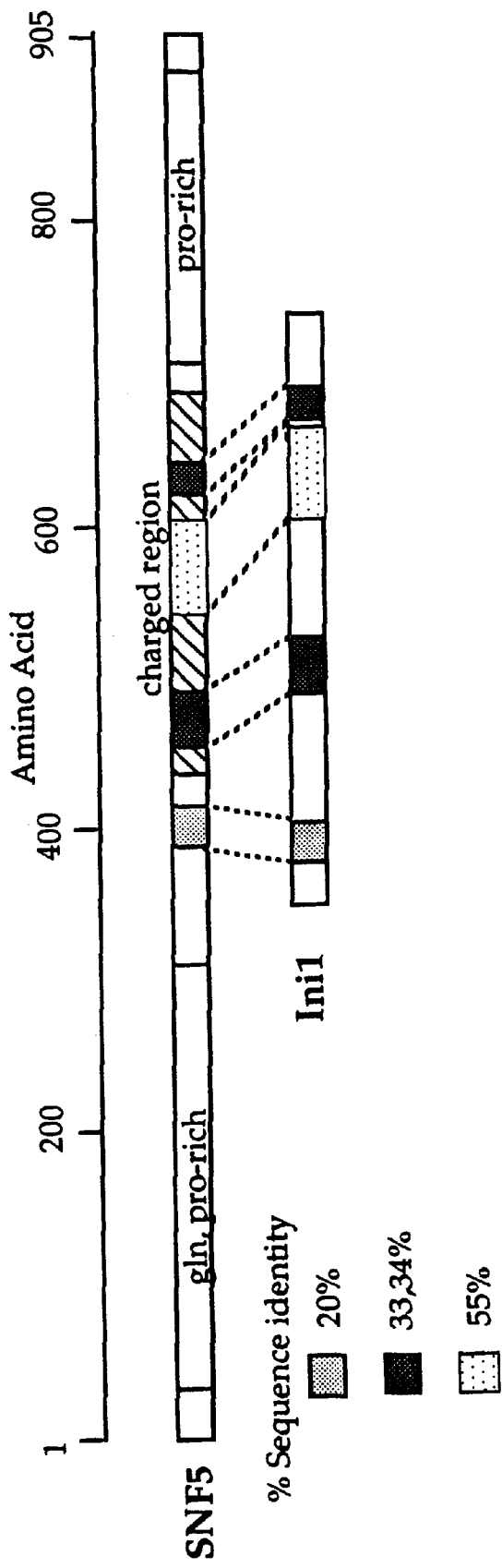

FIG. 5A. Alignment of ini-1 with SNF5. Schematic alignment. The blocks of highest similarity are shaded, and the % identity given below. The glutamine and proline-rich regions of SNF5 are indicated.

FIG. 5B. A central portion of the ini-1 amino acid sequence is shown aligned with that of the yeast SNF5 sequence (SEQ ID NO:3–4). Residues which are identical between the two sequences are indicated by shading. The three regions that show high degree of sequence similarity between the two proteins (33–50% identity) are indicated by the bars underneath.

Figure 6A:
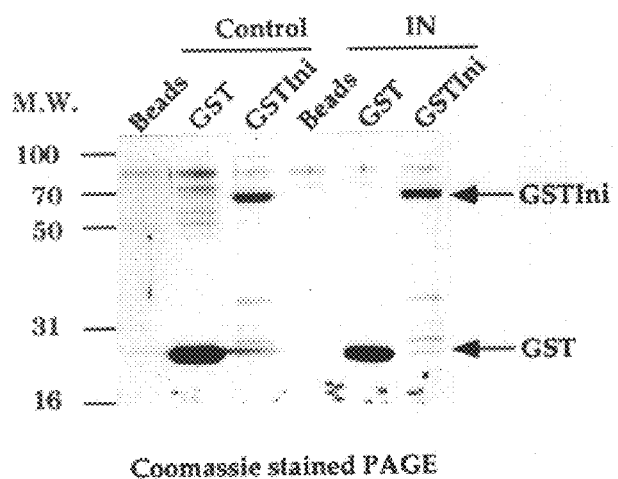

FIG. 6A. Interaction of IN with GST-ini-1 in vitro. Coomassie-stained SDS/PAGE of the recombinant proteins expressed in bacteria and purified by affinity to glutathione-agarose beads.

Figure 6B:
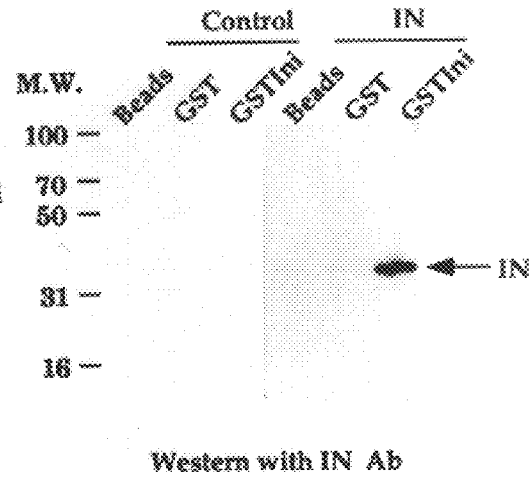

FIG. 6B. Interaction of IN with GST-ini-1 in vitro. The proteins bound to beads were used to specifically bind recombinant IN from a bacterial lysate, and the bound proteins were analyzed by Western blot with IN-specific antibodies. IN: lysate of bacterial cultures expressing IN; control: control bacterial lysate not expressing IN. Beads: glutathione beads alone; GST: GST bound to glutathione beads; GSTIni: GST-ini-1 bound to glutathione beads. The position of the IN protein is indicated by the arrow. Molecular weight standards are indicated on the left.

Figure 6C:
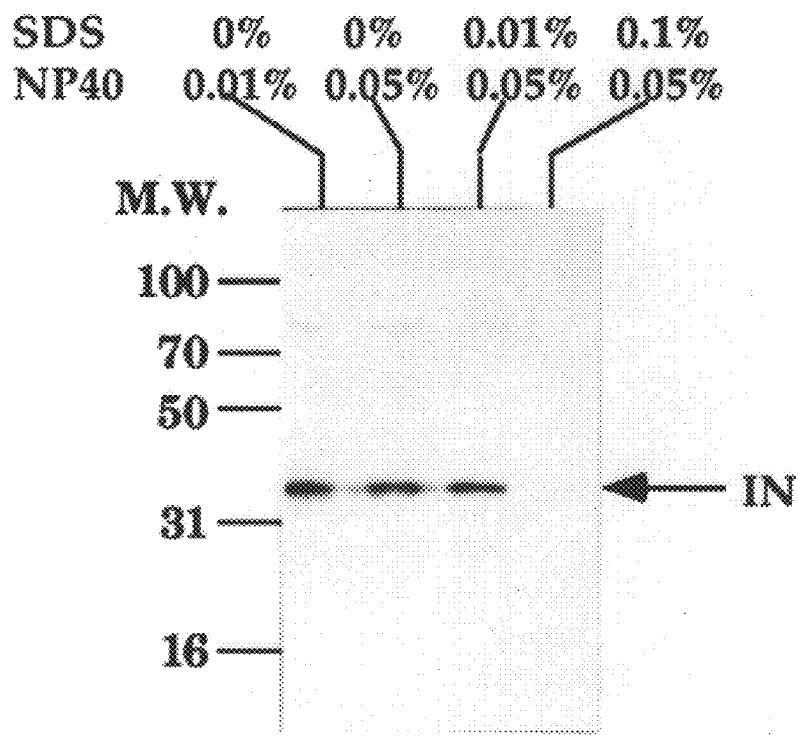

FIG. 6C. Interaction of IN with GST-ini-1 in vitro. Effect of SDS and detergents on IN-Ini interaction. IN-ini-1 complexes on beads were washed with buffer containing various concentrations of SDS and NP-40, and the remaining proteins were analyzed by Western blot with antibodies to IN. The concentration of SDS and NP40 are indicated above each lane.

FIG. 7A. Effect of salt on the interaction of IN with ini-1. Coomassie-stained gel of the bound proteins.

FIG. 7B. Effect of salt on the interaction of IN with ini-1. Western analysis of a duplicate gel using antibodies to IN. Lanes are as in FIG. 7A. Various concentration of NaCl used in the binding assays are indicated above the lanes.

DETAILED DESCRIPTION OF THE INVENTION

This invention provides an isolated nucleic acid encoding an integrase interactor 1 gene (ini-1) (SEQ ID NO.1). In one embodiment of this invention, the isolated nucleic acid is DNA encoding the integrase interactor 1 gene that is free of one or more introns present in genomic DNA. In other embodiments of this invention, the isolated nucleic acid sequence described herein are cDNA or genomic DNA. The DNA may be labelled with a detectable moiety selected from a group consisting of a fluorescent label, a radioactive atom, and a chemiluminescent label.

In one embodiment of the invention replicable vectors which comprise the nucleic acid described herein are also provided. The replicable vectors include those where the nucleic acid is free of introns. Suitable vectors comprise, but are not limited to, a plasmid or a virus.

The DNA sequence described and claimed herein is useful for the information which it can provide concerning the amino acid sequence of the polypeptide. The sequence is useful for generation new cloning and expression vectors, transforming and transfecting prokaryotic, eucaryotic and bacterial host cells, and new and useful methods for cultured growth of such host cells capable of expression of the polypeptide and related products.

The invention further provides a purified polypeptide comprising naturally-occurring ini-1, the polypeptide may be the product of prokaryotic or eukaryotic expression of an exogenous DNA sequence. The exogenous DNA sequence is a cDNA or a genomic DNA sequence. The exogenous DNA sequence may be carried on an autonomously replicating DNA plasmid or viral vectors.

In one embodiment the purified polypeptide of ini-1 may be human ini-1.

The invention also provides for the purified polypeptide possesses part or all the amino acid sequence of human ini-1 as shown in FIG. 4 (SEQ ID NO.2) or any naturally occurring allelic variant thereof. The purified polypeptide may have in vivo or in vitro biological activity of naturally occurring ini-1. The purified polypeptide may be covalently associated with a detectable label substance.

The invention also provides a method of determining whether a compound is capable of interfering with the formation of a complex between a retrovirus integrase protein and an ini-1 protein, which comprise the following steps:

a) incubating the compound with an appropriate ini-1 affinity fusion protein and the retrovirus integrase protein;

b) contacting the incubate of step (a) with an appropriate affinity medium under conditions so as to bind the ini-1 affinity protein complex, if such a complex forms; and c) measuring the amount of the ini-1 affinity protein complex formed in step (b) so as to determine whether the compound is capable of interfering with the formation of the complex between the retrovirus integrase protein and the ini-1 protein.

In one preferred embodiment, the retrovirsus integrase protein may be HIV-1 IN, the affinity fusion protein may be GST-ini-1. The affinity medium may be glutathione-agarose beads. The amount of the affinity protein complex formed may be determined using monoclonal or polyclonal antibodies. The above method may also be performed using a retroviral integrase protein fusion.

In one preferred embodiment the ini-1 affinity protein complex or the retrovirus integrase affinity protein complex is bound to the affinity medium. The ini-1 affinity protein complex or the retrovirus integrase affinity protein complex is purified and removed from the affinity medium and the amount of integrase protein or ini-1 protein is determined. The amount of the integrase protein or ini-1 protein may be determined using monoclonal or polyclonal antibodies. The above assays may be performed in vivo or in vitro.

The invention also provides for a method of disrupting a retrovirus life cycle in a cell which comprises contacting the cell with a compound which is capable of disrupting a retrovirus integrase protein-ini-1 protein interaction so as to thereby disrupt the retrovirus life cycle. The compound contacting the cell may be a soluble ini-1 fragment, a HIV-1 IN fragment or a chemical molecule. The soluble ini-1 fragment may be a small peptide of 4 to 20 amino acids in length, in one preferred embodiment there may be 6 to 12 amino acids. Other fragments may include non-peptide mimics of ini-1 fragments.

A method of disrupting a retrovirus life cycle in a mammal which comprises administering to the mammal a compound which is capable of disrupting a retrovirus integrase protein-ini-1 protein interaction so as to thereby disrupt the retrovirus life cycle. The compound administered to the mammal may be a soluble ini-1 fragment, a HIV-1 IN fragment or a chemical molecule.

The invention provides an isolated cDNA encoding an integrase interactor 1 gene (ini-1) having a coding sequence substantially the same as the coding sequence as shown in FIG. 4.

For the above-identified compounds and methods the retrovirus may be selected from the following groups, Avian leukosisarcoma, Mammalian C-type, B-type viruses, D-type viruses, HTLV-BLV group, Lentiviruses and "Foamy viruses. The retroviruses may also be selected from the following examples, Rous sarcoma virus (RSV), Avian myeloblastosis virus (AMV), Avian erythroblastosis virus (AEV), Rous-associated virus (RAV)-1 to 50, RAV-0, Moloney murine leukemia virus (MO-MLV), Harvey murine sarcoma virus (HA-MSV), Abelson murine leukemia virus (A-MuLV), AKR-MuLV, Feline leukemia virus (FeLV), Simian sarcoma virus, endogenous and exogenous viruses in mammals, Reticuloendotheliosis virus (REV), spleen necrosis virus (SNV), Mouse mammary tumor virus (MMTV), Mason-Pfizer monkey virus (MPMV), "SAIDS" viruses, Human T-cell leukemia (or lymphotropic) virus (HTLV), Bovine leukemia virus (BLV), Human immunodeficiency virus (HIV-1 and -2), Simian immunodeficiency virus (SIV), Feline immunodeficiency virus (FIV), Visna/Maedi virus, Equine infectious anemia virus (EIAV), Caprine arthritis-encephalitis virus (CAEV), Progressive pneumonia virus, many human and primate isolates e.g., simian foamy virus (SFV).

This invention is also directed to pharmaceutical compositions comprising therapeutically effective amounts of compounds of the invention together with suitable diluents, preservatives, solubilizers, emulsifiers and adjuvants. Administering a therapeutically effective amount refers to that amount which provides therapeutic effect for a given condition and administration regime. Such compositions are liquids or lyophilized or otherwise dried formulations and include diluents of various buffer content (e.g., Tris-HCL, acetate, phosphate), pH and ionic strength, additives such as albumin or gelatin to prevent adsorption to surfaces, detergents (e.g., Tween 20, Tween 80, Pluronic F68, bile acid salts), solubilizing agents (e.g., glycerol, polyethylene glycol), anti-oxidants (e.g., ascorbic acid, sodium metabisulfite), preservatives (e.g., Thimerosal, benzyl alcohol, parabens), bulking substances or tonicity modifiers (e.g., lactose, mannitol), complexation with metal ions, or incorporation of the material into or onto particulate preparations of polymeric compounds such as polylactic acid, polyglycolic acid, hydrogels, etc. or into liposomes, microemulsions, micelles, unilamellar or multilamellar vesicles, erythrocyte ghosts, or spheroplasts. Such compositions will influence the physical state, solubility, stability, rate of in vivo release. Controlled or substained release compositions include formulation in lipophilic deposits (e.g., fatty acids, waxes, oils). Also included in this invention are particulate compositions coated with polymers (e.g., poloxamers or poloxamines). Other embodiments of the compositions of the invention incorporate particulate forms protective coatings and permeation enhancers for various routes of administration, including parenteral, pulmonary, nasal and oral.

The following examples are offered to more fully illustrate the invention, but are not to be construed to limit the scope thereof.

Isolation of cDNAs Encoding Proteins That Interact With HIV-1 IN

To identify human proteins that bind to the HIV-1 integrase, the yeast two hybrid system was used to screen a large library of human cDNAs. In this system, the expression of two constructs in yeast—one encoding the GAL4 DNA binding domain (GAL4DB) fused to one protein, and the other encoding the GAL4 activator domain (GAL4AC) fused to another protein—results in the reconstitution of GAL4 function if the two proteins bind with sufficient affinity (Fields and Song, 1989). The appearance of GAL4 function can be detected by monitoring the expression of an integrated reporter gene, such as lacZ, downstream of a GAL4-dependent promotor. Previously the system was used to detect several interactions between viral and host proteins (Luban et al., 1992; Luban et al., 1993), and in particular to detect IN-IN multimerization (Kalpana and Goff, 1993).

To generate a library of GAL4 activator domain-cDNA fusions, the inserted sequences of a human cDNA library derived from the HL60 macrophage/monocytic cell line were excised from the original phage vector and transferred in bulk to a plasmid vector. Six different pools of plasmids were prepared, each containing 100,000 to 500,000 individual clones (Table 1).

TABLE 1

| Library Pools | Number of original E. Coli. Clones | IN-interacting clones recovered |
|---|---|---|
| Pool I | 0.23 × 105 | — |
| Pool II | 0.5 × 105 | One |
| Pool III | 5.00 × 105 | — |
| Pool IV | 3.00 × 105 | — |
| Pool V | 1.5 × 105 | — |
| Pool VI | 1.00 × 105 | Two |

Table 1 is a summary of recombinant clones in various pools of HL60 cDNA library and positive IN-interacting clones obtained from each pool in the two hybrid screen.

Yeast strain GGY1::171, which contains an integrated reporter gene, was transformed with a mixture of a given DNA pool and an equal amount of pGAL4DB-IN DNA, encoding a fusion protein consisting of the GAL4 DNA binding domain and the entire HIV-1 IN (Kalpana and Goff, 1993). Cotransformants were recovered after selection for markers on both plasmid vectors, and colonies were replicated to filters and stained with X-gal. 10 blue colonies were obtained from a total of 600,000 transformants screened (Table 1). The plasmids were rescued from these colonies and retested by transformation along with the plasmid encoding GAL4DB-IN into GGY1::171. Three of these candidate clones consistently tested positive upon cotransformation: one from pool II and two from pool VI. Subsequent analysis of these clones (see below) showed that all three contained identical cDNA inserts. Thus, an single cDNA was identified in this large-scale screen as encoding a protein able to interact with the HIV-1 IN. The novel gene was termed ini-1 for integrase interactor 1.

Specificity of the Interaction Between Novel Sequences and HIV-1 IN

Many cDNAs initially isolated as candidates in the two-hybrid system do not in fact depend on interaction with the partner hybrid protein, but instead activate expression of the indicator gene through other means (Luban et al., 1993). To demonstrate a requirement of the partner for interaction, the GAL4AC-ini-1 fusions were tested for activation in several settings (Table 2).

TABLE 2

| Fusion Proteins | Promoter | Operator | β-gal Activity |
|---|---|---|---|
| GAL4DB-IN + GAL4AC-INI | GAL1 | $UAS_G$ | ++++ |
| GAL4DB-IN + GAL4AC-INI | GAL1 | $UAS_G$ | ++++ |
| GAL4DB-MG + GAL4AC-INI | GAL1 | $UAS_G$ | − |
| GAL4DB + GAL4AC-INI | GAL1 | $UAS_G$ | − |
| GAL4AC-INI | GAL1 | $UAS_G$ | − |
| LexADB-IN + GAL4AC-IN | GAL1 | $UAS_G$ | ++++ |
| LexADB-IN + GAL4AC-INI | GAL1 | $UAS_G$ | ++++ |
| LexADB-lamin + GAL4AC-INI | GAL1 | $UAS_G$ | − |
| LexADB + GAL4AC-INI | GAL1 | $UAS_G$ | − |
| GAL4AC-INI | GAL1 | $UAS_G$ | − |

TABLE 2 shows the specificity of IN-ini-1 interaction in yeast under various conditions of promoters and DNA binding domains. Two plasmids, one encoding GAL4DB fusion and the other encoding GAL4AC fusions were co-transformed into either GGY1::171 (for testing the GAL4DB fusions) or CTY10-5d (for testing LexADB fusions). The transformants were scored for b-gal activity. Fusion protein GAL4DB-IN was encoded by plasmid pMAI, GAL4AC-IN by pGADI, GAL4AC-INI by pD2.1, LexADB by pSH2-1, LexADB by pSHIN, and LexADB-IN by pSHIN, and LexADB-lamin by pLexAlamin.

Transformation of GGY1::171 by the GAL4AC-ini-1 plasmids alone, without pGAL4DB-IN, did not activate lacZ expression. Cotransformation with a plasmid encoding GAL4DB alone also did not activate, suggesting that the ini-1 protein did not interact directly with the GAL4 DNA binding domain. To confirm that the activation was not restricted to the GAL4 system, the DNAs were introduced into strain CTY10-5d, containing an integrated GAL1-lacZ fusion downstream of the lexA operator, along with a plasmid encoding a LexA-IN fusion, or as control, LexA alone. LacZ expression was detected only when the GAL4AC-ini-1 protein was present with LexA-IN fusions and not with the LexA protein alone. These results indicate that activation by ini-1 fusions was not dependent on the particular operator and binding domain used to tether the IN protein to DNA.

To determine whether the ini-1 protein could interact with unrelated fusion proteins, the three ini-1 plasmids were introduced into the appropriate indicator strain along with control plasmids encoding a GL4DB-Moloney gag fusion or a lexA-Lamin fusion protein. No lacZ expression was detected in either of these settings, indicating that activation by the cDNA fusions was specific for the HIV-1 IN protein (Table 1). Thus, in contrast to other screens for interacting partners with other proteins, where many RNA-binding proteins were initially detected, there were no false positive clones recovered with IN. The results suggest that the original GAL4-IN construct was not prone to interaction with false positives, but bound uniquely to a human protein encoded by a single cDNA.

The Central Domain of IN is Required for Interaction With ini-1

Figure 1:
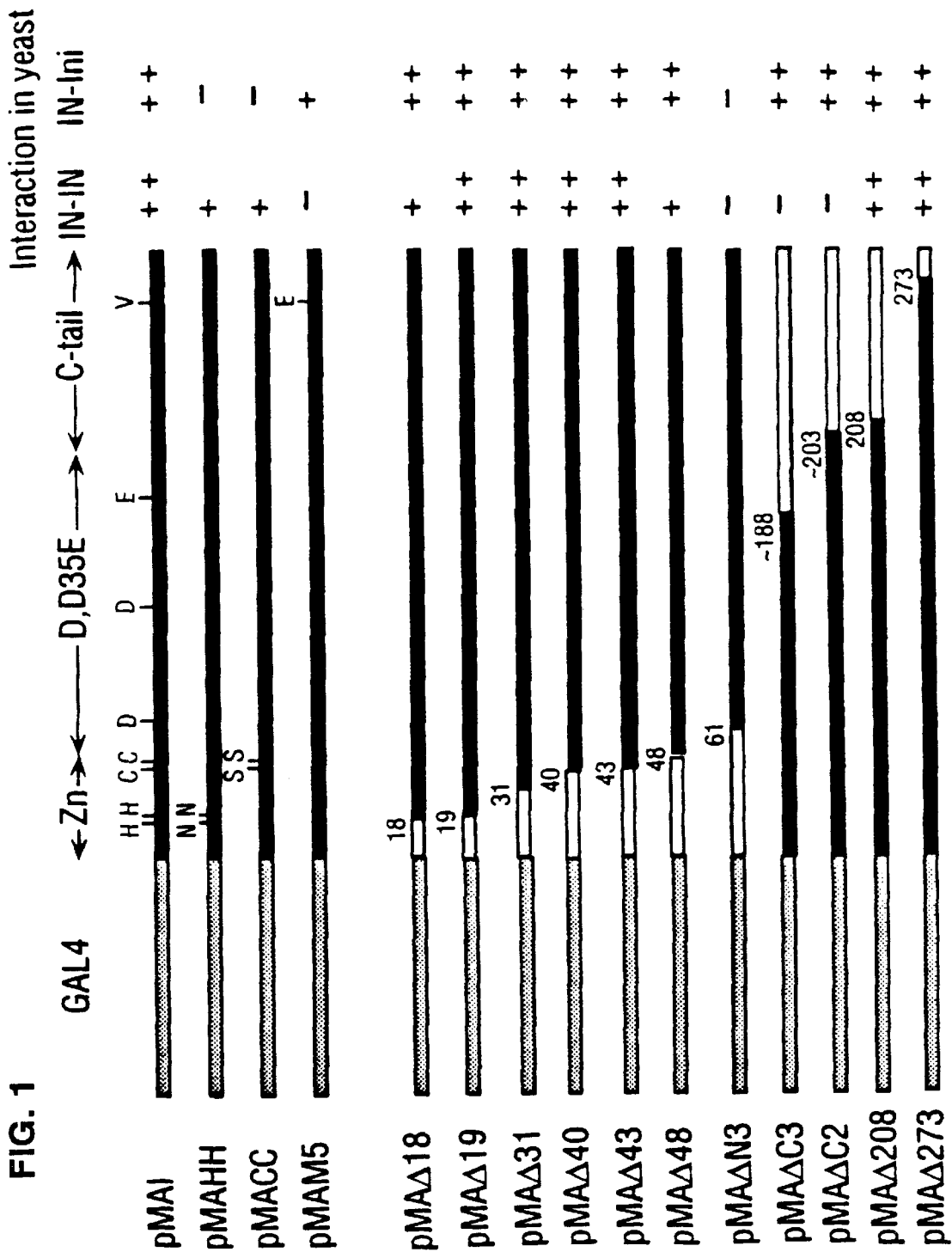
FIG. 1. Interaction of IN mutants with ini-1. Bars in the diagram indicate the regions retained in various GAL4DB-IN mutants tested for their ability to interact with a GAL4AC-ini-1 fusion in the yeast strain GGY1::171. Yeast were cotransformed with plasmids encoding each GAL4DB fusion and GAL4AC-ini-1 and assayed for the production of β-galactosidase. Deletions pMAΔ18-273 (Kalpana and Goff, 1993) were tested for IN-IN interaction in the context of GAL4AC fusions along with a GAL4DB-IN fusion. The rest of mutants were tested for IN-IN interactions when fused to either GAL4DB or GAL4AC and against a partner containing either the same mutant or the wild-type IN; the indicated result was obtained in all these settings. Gray bars indicate the GAL4 portion of the fusion protein; black portions indicates the IN portion; the blank portion of the bar indicates the deleted portion. The substitution mutations are indicated by the residues on top of the relevant bar. The residues are H=His, C=Cys, D=Asp, E=Glu, V=Val, N=Asn and S=Ser. The deletion junctions are indicated by the residue at the junction. '++'=dark blue; '+'=blue; '−'=white colony phenotype in the X-Gal assay.

The two hybrid system has been previously used to define the minimal region of IN required for IN-IN interactions, finding that the central core region of the protein was necessary for multimerization (Kalpana and Goff, 1993). To determine the region of IN required for binding to ini-1, a panel of mutants of pGAL4DB-IN were tested containing deletions and point mutations for activation in the presence of GAL4AC-ini-1. Mutants lacking either the N-terminal domain of IN, containing a putative zinc finger region, or the C-terminal domain, retained their ability to bind to ini-1 (FIG. 1). Two larger C-terminal deletions, removing part of the central core and eliminating IN-IN interactions, did not affect In-ini-1 interaction. In addition, a variant containing a point mutation in the C-terminal region of IN that blocked IN-IN interaction (Kalpana and Goff, unpublished date) was still positive for IN-ini-1 interaction. Thus, the IN-ini-1 interaction requires less of the IN central and C-terminal domains than the IN-IN interaction. Two mutants of IN with point mutations in the N-terminal zinc finger region were also tested. While these mutants still carry out IN-IN interactions, they were both defective for the In-ini-1 interaction. Thus, binding to ini-1 seems to require the N-terminal zinc finger region of IN. While the two interaction domains—that for IN-IN dimerization and that for In-ini-1 interaction—may overlap, the IN-ini-1 domain seems to be more N-terminal.

Expression of the ini-1 mRNA in Mammalian Cells

Figure 2B:
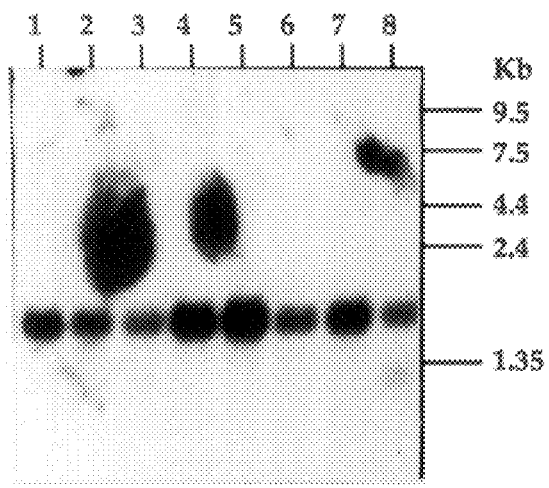
FIG. 2B. The blot of FIG. 2A after stripping and reprobing with a human actin cDNA probe.
Figure 2C:
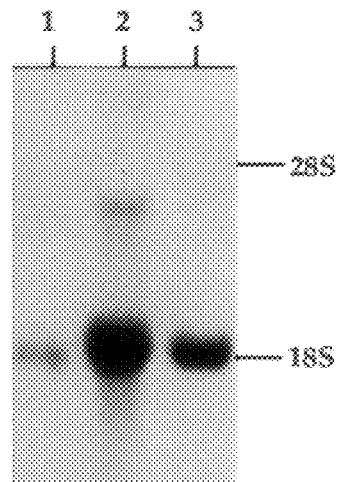
FIG. 2C. Northern analysis of human cell lines.
Figure 2A:
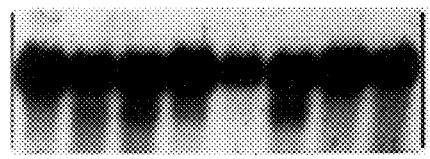
FIG. 2A. Northern analysis of human tissues. Northern blot probed with ini-1 cDNA insert isolated from pD2.1. Each lane contains about 2 ug of poly(A)-selected mRNA. Lane 1: peripheral blood lymphocytes; 2: colon; 3: small intestine: 4:ovary; 5: testis; 6: prostate; 7: thymus; 8: spleen.

The cDNA inserts recovered in the GAL4AC plasmids were derived from mRNAs of the HL60 human monocytic-myelocytic cell line, suggesting that the gene must be expressed in at least moderate levels in this tumor line. The sequences present in the cDNA insert might include only a portion of the complete mRNA. To determine how widely the ini-1 mRNA was expressed, and to determine the size of the full-length transcript, RNAs were isolated from HeLa cells, a human B-cell tumor line (CB33), and a human T-cell line (Hut78), and analyzed by Northern blot hybridization using an ini-1 probe (FIG. 2). RNAs from all three lines contained a single major species detected with the probe, migrating at approximately 2.0 kb. In addition, the HeLa and CB33 lines contained a minor species migrating at approximately 4.0 kb. To determine whether the ini-1 gene was expressed in normal tissues, RNAs isolated from peripheral blood lymphocytes, colon, small intestine, ovary, testis, prostate, thymus and spleen were separated by electrophoresis, blotted and probed as before (FIG. 2). All 8 tissues expressed substantial levels of the 2.0 kb mRNA. The level of expression of the mRNA was similar in all the tissues tested. In addition to the major mRNA species, long exposures of the autoradiographs revealed low levels of a species migrating at 1.25 kb present in the spleen, and similarly low levels of a species migrating at about 4 kb in the thymus, prostate and testes. These results suggest that the ini-1 gene is very widely, and possibly ubiquitously, expressed, and that the major transcript in all tissues is approximately 2.0 kb in length. Additional transcripts with alternative structures, or transcripts from closely related genes, may be present in some tissues.

Isolation of cDNAS Spanning the Complete ini-1 Coding Region and Predicted Sequence of the ini-1 Protein The cDNA inserts in the three GAL4AC plasmids recovered were examined by restriction mapping and partial sequence analysis, and all were found to consist of the identical 1.0 kb fragment, presumably from sibling clones in the original phage library. To isolate longer cDNAs, this fragment was excised from the plasmid and used as a probe to screen two phage cDNA libraries of HeLa cell mRNA, one made in the λZapII vector and one in λgt11. 20 clones were recovered from approximately 600,000 clones of the λZapII library, and the six largest inserts were excised from the vector. Four of these had overlapping restriction maps (FIG. 3) consistent with that of the probe DNA and were subjected to sequence analysis. 12 clones were recovered from the λgt11 library but no inserts were larger that the earlier clones; one of these cDNAs was also sequenced. The DNA sequences obtained could be readily aligned, and spanned 1.85 kb, nearly the size of the full-length mRNA detected by Northern blots (FIG. 3).

The DNA sequence from the clones contained several unusual features (FIG. 4) (SEQ ID NO.1). First, the sequence was extraordinarily GC-rich and included several long stretches of pure GC runs. These features made determination of the sequence by dideoxynucleotide methods difficult, and several regions could only be read from smaller subclones that presumably removed secondary structures from the DNA templates. The sequence revealed a single long open reading frame of 385 codons, curiously beginning with a tandem array of four consecutive ATG codons. The first ATG of the array lies in a good match to the consensus sequence for translational initiation (Kozak, 1991). These codons are likely to represent the rue start sites for translation, since termination codons are found upstream of these ATGs. The significance of the presence of these tandem methionine codons remains unclear. The one clone from the λgt11 library (pINI.gt) contained a stretch of poly(A) residues at the 3' junction adjacent to the vector, and three of the clones from the λZAPII library had 3' junctions at or upstream of this position, such that they could have been derived from a similar mRNA. Examination of the sequence upstream of the poly(A) stretch revealed the presence of a perfect consensus polyadenylation signal, AATAAA, at −25 bp relative to the poly(A). These results suggest that most of the ini-1 mRNAs are processed by cleavage and polyadenylation at this position. One cDNA clone (pINI.21), however, extended beyond this region without poly(A) sequences. This clone suggests that some mRNAs are of extended length and arise through use of alternative poly(A) addition sites further downstream. These RNAs could possibly account for the longer mRNAs observed in Northern blots of mRNAs from various tissues. One clone, (pINI.9), lacked a short stretch of 27 bp (nt 206–232) near the 5' end of the coding region. This clone might have arisen from an alternatively spliced mRNA lacking an internal exon.

The long open reading frame predicts the formation of a protein of 44,131 daltons containing 385 amino acids. The sequence revealed the presence of a heptad repeat of three leucine residues near the amino-terminus of the encoded protein; these residues could potentially form a leucine zipper structure. While these sequences might be important for multimimerization, interactions with other proteins, or for the normal function of the ini-1, these structures can be eliminated as important for interaction with the IN protein since they are not present in the original yeast plasmid clone that demonstrated binding to IN. The predicted sequence includes no amino-terminal secretion signals, no transmembrane segment, and no strikingly acidic or basic regions. There are three potential sites for addition of N-linked sugars (FIG. 4). The predicted pI of the protein is 6.15.

ini-1 has Sequence Similarity to SNF5

Comparison of the predicted sequence of ini-1 with the known sequences in the GenEmbl data base revealed a single significant match, the SNF5 protein of *S. cerevisiae*, encoding a transcriptional activator protein (Abrams et al., 1986; Laurent et al., 1990; Neigeborn and Carlson, 1984). SNF5 is a nuclear protein thought to act in a complex with several other proteins including SNF2/SWI2, SNF6, SWI1, and SWI3, to activate target gene expression (Laurent et al., 1991; Peterson and Herskowitz, 1992). The alignment of ini-1 with the SNF5 sequence displayed three regions of close similarity, with 33–55% sequence identity and 41–71% of conserved residues (FIG. 5). All three regions lay in the central portion of the SNF5 sequence rich in changed amino acids and the flanking N-and C-terminal portions of the yeast gene were not conserved in the human gene. In particular, the proline- and glutamine-rich segments of the yeast protein were not retained. Based on the striking similarity between the yeast and human genes in the core coding region, the ini-1 may be a human homologue of the yeast SNF5 gene.

IN Binds to ini-1 in vitro

To demonstrate that ini-1 interacts directly with IN in solution, binding studies between recombinant proteins were carried out in vitro. The ini-1 cDNA from plasmid pD2.1 was inserted into plasmid pGEX and expressed as a glutathione S-transferase fusion protein in $E.\ coli$. Lysates of the bacteria were prepared, and the GST-ini-1 protein was affinity purified on glutathione agarose beads (G-beads). The beads were washed extensively to remove nonspecific proteins. To ensure that the GST-ini-1 proteins were successfully expressed and bound to the beads, the proteins on the beads were recovered by boiling in SDS, and examined by SDS-PAGE (FIG. 6A). A novel protein of the expected size (60 kd) was recovered from lysates containing the GST-ini-1 protein, and represented 70–80% of the total protein.

The immobilized ini-1 was used as an affinity matrix for binding of IN. The HIV-1 In protein was expressed in $E.\ coli$ from the T7 promoter after induction of the T7 polymerase, and soluble IN protein was extracted from inclusion bodies with buffer containing high salt. These lysates were then incubated with G-beads alone, G-beads with GST alone, or G-beads with GST-ini-1, the beads were washed extensively, and the bound proteins were recovered with SDS. The eluted proteins were separated by SDS-PAGE, blotted to nitrocellulose, and visualized with polyclonal antibodies specific for HIV-1 IN (FIG. 6B). The results showed that the recombinant IN bound efficiently to the ini-1 beads and not to the control GST beads or the beads alone.

To further characterize the IN-ini-1 interaction, binding experiments were repeated under various conditions (FIGS. 6B and 6C). Binding was observed over a wide range of salt concentrations, and was detected even in the presence of 1 M NaCl. The IN was retained by the ini-1 beads when washed with buffers containing 0.5% NP40 or 0.1% Triton X-100. The interaction was disrupted, however, by the addition of 0.1% SDS, suggesting that denatured IN and ini-1 proteins could not bind.

ini-1 acts as a Transcriptional Activator in Yeast When Expressed as a DNA Binding Domain Fusion Protein The yeast SNF5 protein is a transcriptional activator, required for the high-level of expression of many genes in yeast. Though the protein has not been shown to bind to DNA directly, it is capable of activating a reporter gene when artificially tethered to DNA by fusion to the lexA DNA binding domain (Laurent et al., 1990). To determine whether ini-1 could also act as a transcriptional activator in this setting, a construct encoding a fusion of GAL4 DNA binding domain-ini-1 was generated and expressed in an indicator strain containing a GAL1-lacZ reporter. The transformants expressed high levels of β-galactosidase as judged by staining with χ-gal, while control transformants expressing only the GAL4DB or GAL4AC-ini-1 protein did not. Thus, like SNF5, the human ini-1 protein can activate transcription in yeast.

The ini-1-IN Interaction

The two-hybrid system has been used to seek human proteins that might be involved in retroviral replication. The novel gene identified in this screen, ini-1, encodes a protein which is capable of binding the HIV-1 IN both in vivo and in vitro. The fact that all three clones recovered in the screen were identical, and that no other clones were identified in a large number tested, suggests that ini-1 is the major human protein capable of binding to IN. It is noteworthy that there were no false positive clones at all detected in this screen, suggesting that the GAL4DB-IN fusion used here did not allow interactions to the GAL5 region or other proteins that often produce false positives. The binding seemed to be very specific, and could be observed in the setting of several fusion constructs including either the GAL4 or LexA binding domains. The interaction measured in vitro was tight and was resistant to high salt, suggesting that it may involve hydrophobic contacts on the two partners. The binding in solution was also specific, with no significant binding of IN to GST or GST-cyclophilin proteins (Luban et al., 1993) tested as controls.

The region of IN required for binding to ini-1 was a portion of the central domain; the very N-and C-terminal regions were dispensable. The essential region for interaction to ini-1 was distinct from that for multimerization of IN, apparently lying more toward the N-terminus of the protein. Mutants of IN that showed differential effects on the two interactions were readily obtained. It is possible that the ini-1 protein can bind to a multimer of IN and stabilize multimer formation, or it could block or compete for IN multimerization. ini-1 could stimulate concerted joining of both termini into target DNAs, accelerating functional integration reactions; or, alternatively, it could inhibit concerted joining of two termini of the viral DNA to the target sequence, acting to restrain normal retroviral integration. The function of ini-1 can be explored through analysis of its effects on various in vitro integration activities.

Targeting Retroviral Integrations

The presence of a protein like ini-1 in an infected cell able to bind the HIV-1 IN could be responsible for targeting proviral insertion to selected sites in the genome. The phenomenon of non-random integration of retroviral and retrotransposon DNAs is well-established, but the mechanisms by which targeting occurs remain uncertain. Insertions seem to preferentially occur into transcriptionally active regions, and perhaps into open chromatin (Rohdewohld et al., 1987; Vijaya et al., 1986). In the case of the yeast transposon Ty3, site selection is profoundly specific, with insertions almost always occurring at a position 16 or 17 bp from the site of initiation of polIII transcripts (Chalker and Sandmeyer, 1990; Chalker and Sandmeyer, 1992). Analysis of mutant promoter sequences and of hybrid target sites strongly suggest that nuclear protein complexes including TFIII1A, TFIIIB, and TFIID are responsible for site selection, and for precise positioning of the insertion into the promoter (Sandmeyer et al., 1990). In the case of the transposon Ty1, site selection is more relaxed, but analysis of a large number of insertions into yeast chromosme III suggests that insertions tend to occur within regions clustered within 400 bp of polIII genes (Ji et al., 1993). Such preferences might be mediated by the accessibility of stretches of DNA, or by interactions of the transposon-IN complex with chromatin of other DNA-bound proteins. The existence of a mammalian protein with high affinity for the HIV-1 IN is consistent with its playing a similar role in site selection for retroviral insertion.

Function of the ini-1 Protein: Reorganization of Chromatin Structure

SNF5 is a transcriptional activator in yeast, and is required for transcription of many unrelated genes such as SUC2, HO, INO1, PHO5, and GAL1, 7 and 10. In addition, it is required for the function of many gene-specific activators, including GAL4, Bicoid, and the glucocorticoid receptor (Laurent and Carlson, 1992; Yoshinaga et al., 1992). Genetic experiments suggest that the yeast SNF5 protein acts in a enormous complex with the products of the SWI1, SNF2/SWI2, SWI3, SNF6, and possibly other genes (Laurent et al., 1991; Peterson and Herskowitz, 1992), and co-immunoprecipitation studies using antibodies to yeast SNF5 confirm its presence in a large complex. The SNF2 subunit of the complex has domains similar in sequence to DNA helicases (Davis et al., 1992; Laurent et al., 1992), and has been shown to exhibit DNA-dependent ATPase activity (Laurent et al., 1993). Mammalian homologues of the yeast SNF2/SWI2 products have recently been identified (Khavari et al., 1993; Muchardt and Yaniv, 1993; Okabe et al., 1992)

The SNF and SWI transcription factors may act by helping to reorganize chromatin structure (for review, see Winston and Carlson, 1992). Deletions of one copy of the genes encoding histones H2A and H2B can suppress the defects in Ty and SUC2 transcription caused by snf2, and 5 mutations (Clark-Adams et al., 1988; Happel et al., 1991), and these suppressors probably act by inducing changes in the chromatin structure as assayed by microccal nuclease digestion experiments (Hirschhorn et al., 1992). Other suppressors of snf and swi mutations have been identified as alleles of a gene encoding histone H3 (cited in Peterson and Herskowitz, 1992), and of a gene encoding a nonhistone DNA binding protein similar to HMG1 (Kruger and Herskowitz, 1991). These observations suggest that the normal role of the SNF and SWI genes may be to alter the arrangement of nucleosomes on target genes to facilitate their transcription. The unexpected sequence similarity of the ini-1 protein to SNF5 is intriguing: the similarity implies that ini-1 may be a novel transcriptional activator in human cells, and may act in a complex to decondense chromatin. The ability of the human sequence to activate a reporter gene in yeast when tethered to DNA lends further support to this notion. Such a role is also consistent with its affinity for HIV-1 IN, and would suggest that ini-1 might indeed account for the propensity of retroviral DNA to insert into active genes.

Finally, the identification of a host protein as interacting with the HIV-1 IN raises the possibility that it may be used as a novel route to inhibit viral replication. If the protein serves to stimulate integration, then drugs which could block the ini-1-IN interaction might retard viral spread. In addition, it might be possible to generate dominant negative alleles of ini-1, perhaps encoding small fragments of the protein, that bind inappropriately to IN and block its activity.

The retroviral integrase protein (IN) is responsible for the insertion of the viral DNA into host chromosomal targets. The two hybrid system has been used to screen a human cDNA library expressed as GAL4 fusion proteins in yeast for gene products that interact with the human immunodeficiency virus type 1 IN. The screen led to the recovery of three independent isolates of the same gene from approximately $10^6$ colonies. The protein encoded by this gene bound tightly to the HIV-1 integrase in vitro. The sequence of the gene suggests that the novel protein is a human homologue of yeast SNF5, a transcriptional activator required for high level expression of many genes. The new gene is termed ini-1 (SEQ ID NO.1) for integrase interactor 1, encodes a nuclear receptor for incoming viral integration complexes, and may be a component of the long-sought mechanism for biased target site selection during provirus integration.

Bacterial and yeast strains: Yeast strain GGY1::171 (MAT αleu2-3,112 his3-200 met-tyrl ura3-52 ade2 gal4Δ gal80Δ URA3::GAL1-lacZ) (Fields and Song, 1989) contains an integrated GAL1-lacZ reporter gene; CTY 10-5d (MATa ade2 trp1-901 leu2-3, 112 his3-200 gal80-URA3::LexA-LacZ) contains an integrated GAL1-lacZ gene with lexA operator. β-galactosidase assays, both in liquid cultures and on nitrocellulose lifts, were carried out as published with minor modifications (Chien et al., 1991). *E. coli* strains DH5α (BRL), XL1blue and SURE (Stratagene) were used for subcloning plasmids; strain BL21(DE3) was used for the expression of recombinant proteins from T7 promoters.

Construction of various recombinant plasmids:

Construction of plasmids pMAI (encoding GAL4DB-IN fusion), and PGADI (encoding GAL4AC-IN), pSHIN (LexADB-IN fusion) and PMA-MG (encoding the GAL4DB fused to the Moloney MuLV Gag protein) have been previously described (Kalpana and Goff, 1993; Luban et al., 1992). Plasmids pGVK10 (expressing the GST-ini-1 fusion protein) and pMAI (expressing GAL4DB-ini-1) were constructed by transfer of the EcoRI cDNA fragment of the interacting clone pD2.1 to the unique EcoRI sites of pGEX-1λT and pMA424, respectively. Construction of IN mutants pMAHH, pMACC, pMAΔN3, pMAΔC2 and pMaΔC3 were described earlier (Kalpana and Goff, 1993). The remaining IN deletion mutants, pMAΔ18 to pMAΔ273, were originally isolated as GAL4AC fusion mutants that retained the ability to interact with GAL4DB-IN. The BamHI-SalI fragments from these mutants were excised from the GAL4AC plasmid and transferred into pMA424. Isolation of pMAM5, encoding a mutant IN defective for IN-IN interaction, will be described elsewhere.

Construction of HL60 cDNA library fused to the activation domain of GAL4:

The HL60 cell cDNAs were excised from a λZap HL60 cDNA library (Stratagene catalogue # 936214). The original λZap library encompassed about a million recombinant phage clones. To ensure that complexity of the original library was retained, a plate lysate of the phage library was prepared by plating $10^7$ phage; phage particles were isolated by PEG precipitation and two consecutive steps of CsCl gradient centrifugation. DNA was isolated from the total phage by standard methods. About 100 μg of DNA was digested with NotI and XhoI, separated on agarose gels and inserts 0.2–3.0 kb in size were isolated by electroelution. The cDNA inserts were ligated to the pGADNot vector (Luban et al, 1993) digested with NotI plus SalI and phosphatase-treated. DH5α cells were transformed with the ligation products and the transformants from six individual batches of 100,000 to 500,000 colonies each were pooled separately in LB/Amp (KGLI, pool I to Pool VI). This unamplified library in pGADNot vector was aliquoted into small vials and stored frozen until further use. The ration of non-recombinants to recombinants in the library was determined by comparing the number of transformants obtained with self ligated vector to that obtained with vector ligated to insert; and by examining plasmids from several individual colonies to determine the presence of insert. Both these tests indicated that there were >95% recombinants in the library. The plasmid library DNA was isolated from 1 l cultures of each pool by Quiagen columns. This DNA was used for transformation into yeast strain GGY1::171.

Transformation of Yeast and Screening for Interacting Clones

Overnight cultures of GGY1::171 were diluted 1:50 or 1:100 in YPAD (YEPD supplemented with 30 μg/ml of adenine) and incubated at 30° C. until the $OD_{600}$ reached 0.25–0.4. The cells were pelleted, washed once with 1/10th volume of 100 mM LiAc/10 mM TE, and resuspended in 1/200th volume of the same buffer. The cells were further incubated with shaking for 1 hour at 30° C. The competent cells were incubated with 1–10 μg of plasmid DNAs encoding GAL4DB and GAL4AC fusions, 20 μg of sonicated salmon sperm carrier DNA (Sigma, catalogue # D-9156) and 40% PEG in LiAC/TE with agitation at 30° C. for 30 minutes. After the PEG treatment, the cells were pelleted and resuspended in 1 ml of YPAD and incubated further for 1 hour at 30°. The post-incubation step increased the efficiency of co-transformation by about 10 fold. Cells were pelleted, resuspended in TE and plated on selective medium.

In vitro Binding of GST-ini-1 Fusion Protein to HIV-1 IN

Bacterial extracts containing GST-ini-1 fusion protein were prepared as follows. Overnight bacterial cultures containing the required plasmid was diluted 1:10 into LB/Amp and incubate at 37° C. until the $O.D._{600}$ was ~0.5. IPTG (isopropyl-β-D-thiogalactopyranoside) was added to a final concentration of 1 mM and incubation was continued for 3–5 hours. The cells were collected and resuspended in buffer Y (50 mM Tris/Cl pH 7.5, 50 mM NaCl, 1 mM EDTA, 0.5% NP-40 and 1 mM PMSF). Lysozyme was added to a final concentration of 1 mg/ml and incubation was continued on ice for half an hour. This lysate was subjected to sonication (3×30 sec bursts). The lysate was clarified in a microfuge for 15 minutes, and the supernatant was transferred to a fresh microfuge tube. Pre-swollen G-beads were added to the above lysate and incubated at 4° C. for 30 minutes with gentle rocking. The beads were spun at 1600 RPM in the microfuge for 20 sec and the resulting pellet was washed three times with excess of buffer Y and resuspended in buffer Y to yield a 50% (v/v) slurry.

Bacterial extract containing HIV-1 IN was prepared as follows. Overnight bacterial cultures of BL21(DE3) containing either one of the plasmids, pT7f11-IN (encodes IN under the control of T7 promoter), and pT7-ΔIN (control plasmid from which In is deleted) were diluted 1:10 in LB/Amp and incubated at 37° C. for 1 hour. IPTG was added to a concentration of 1 mM and incubation was continued for 3–5 hours. The cultures were pelleted and the pellets were resuspended in buffer Y. Lysozyme was added to a final concentration of 1 mg/ml and the cells were incubated on ice for 30 minutes. The lysed bacteria were sonicated and passed through a syringe with a 23 Gauge needle several times. The insoluble material was collected by centrifugation and resuspended in buffer containing 1 M NaCl and 1 mM DTT, and the mixture was subjected to gentle rocking at 4° C. for 30 minutes. The resulting solution was spun in the microfuge for 30 minutes and the supernatant, referred to as 1M NaCl extract of IN, was used for the binding assay with GST-ini-1.

The binding of IN to GST-ini-1 was tested by adding the washed G-beads with bound GST-ini-1 to the 1M NaCl extract of IN and incubating for 30 minutes at 4° C. in buffer containing 1 M Hepes, pH 7.3, 200 mM NaCl, 5 mM DTT, 0.1%f NP-40, 1 mM PMSF and 10 mg/ml BSA. To test the effect of salt, the concentration of NaCl was varied in the binding buffer from 200 mM to 1 M. The mixture was incubated at 4° C. for 30 minutes and washed three times with excess of either buffer Y or buffer Y containing various concentrations of NP-40 and SDS. The resulting beads were boiled in Laemmli buffer and subjected to SDS-PAGE in duplicate. The presence or absence of IN in these binding experiments was determined by Western analysis using monoclonal antisera to IN.

Screening the Phage Library to Isolate Full Length Recombinant Clones of ini-1

Two HeLa cDNA libraries, one constructed in λZap II vector (Stratagene, Cat. #936201) and one constructed in λgt11, were screened using standard methods. The cDNA insert from one positive interacting clone obtained in the yeast screen was purified, labelled by random priming with $^{32}$P-dCTP, and used as a probe to screen about $0.5 \times 10^6$ phage of the λZapII library. DNA isolated from twenty positive cones obtained after three rounds of plague purification was subjected to restriction analysis. Six positive clones that had the largest inserts were chosen for further analysis. The recombinant pBluescript phagemids from these six positive λZapII clones were subjected to in vivo excision using the M13 helper phage (Exassist/SOLR system, Stratagene, Cat #200253).

mRNA Analyses

Unfractionated mRNA prepared from HeLa, CB33 and Hut78 cell lines were subjected to Northern analysis using standard methods. A northern Blot of human mRNAs from multiple tissues (Clontech, Palo Alto, Calif.; catalog #7759-1) was hybridized to a labelled ini-1 probe using standard methods (Maniatis et al., 1982).

References

Abrams, E., Neigeborn, L., and Carlson, M. (1986). Molecular analysis of SNF2 and SNF5, genes required for expression of glucose-repressible genes in S. cerevisae. Mol. Cell. Biol. 6, 3643–3651.

Bushman, F. D., and Craigie, R. (1991). Activities of human immunodeficiency virus (HIV) integration protein in vitro: specific cleavage and integration of HIV DNA. Proc. Natl. Acad. Sci. USA 88, 1339–1343.

Bushman, F. D., Fujiwara, T., and Craigie, R. (1990). Retroviral DNA integration directed by HIV integration protein in vitro. Science 249, 1555–1558.

Chalker, D. L., and Sandmeyer, S. B. (1990). Transfer RNA genes are genomic targets for de novo transposition of the yeast retrotransposon Ty3. Genetics 126, 837–850.

Chalker, D. L., and Sandmeyer, S. B. (1992). Ty3 integrates within the region of RNA polymerase III transcription initiation. Genes Dev. 6, 117–128.

Chien, C.-T., Bartel, P. L., Sternglanz, R., and Fields, S. (1991). The two hybrid system: A method to identify and clone genes for proteins that interact with a protein of interest. Proc. Natl. Acad. Sci. USA 88, 9578–9582.

Clark-Adams, C. D., Norris, D., Osley, M. A., Fassler, J. S., and Winstron, F. (1988). Changes in histone gene dosage alter transcription in yeast. Genes Dev. 2, 150–159.

Craigie, R., Fujiwara, T., and Bushman, F. (1990). The IN protein of Moloney murine leukemia virus processes the viral DNA ends and accomplishes their integration in vitro. Cell 62, 829–837.

Davis, J. L., Kunisawa, R., and Thorner, J. (1992). A presumptive helicase (MOT1 gene product) affects gene expression and is required for viability in the yeast Saccharomyces cerevisiae. Mol. Cell. Biol. 12, 1879–1892.

Dhar, R., McClements, W., Enquist, L., and Vande Woude, G. (1980). Nucleotide sequences of integrated Moloney sarcoma provirus long terminal repeats and their host and viral junctions. Proc. Natl. Acad. Sci. USA 77, 3937–3941.

Farnet, C. M., and Haseltine, W. A. (1991). Determination of viral proteins present in the human immunodeficiency virus type 1 preintegration complex. J. Virol. 65, 1910–1915.

Fields, S., and Song, O.-K. (1989). A novel genetic system to detect protein-protein interaction. Nature 340, 245–246.

Fields, S., and Song, O.-K. (1994). System To Detect Protein-Protein Interactions. U.S. Pat. No. 5,283,173.

Fujiwara, T., and Mizuuchi, K. (1988). Retroviral DAN integration: structure of an integration intermediate. Cell 54, 497–504.

Goff, S. P. (1992). Genetics of retroviral integration. Annu. Rev. Genet. 26, 527–544.

Happel, A. M., Swanson, M. S., and Winston, F. (1991). The SNF2, SNF5, and SNF6 genes are required for Ty transcription in Saccharomyces cerevisiae. Genetics 128, 69–77.

Hirschhorn, J. N., Brown, S. A., Clark, C. D., and Winston, F. (1992). Evidence that SNF2/SWI2 and SNF5 activate transcription in yeast by altering chromatin structure. Genes Dev. 6, 2288–2298.

Hughes, S. H., Shank, P. R., Spector, D. H., Kung, H.-J., Bishop, J. M., Varmus, H. E., Vogt, P. K., and Breitman, M. L. (1978). Proviruses of avian sarcoma virus are terminally redundant, co-extensive with unintegrated linear DNA, and integrated at many sites. Cell 15, 1397–1410.

Hwang, L. H., and Gilboa, E. (1984). Expression of genes introduced into cells by retroviral infection is more efficient than that of genes introduced by DNA transfection. J. Virol. 50, 417–424.

Ji, H., Moore, D. P., Blomberg, M. A., Braiterman, L. T., Voytas, D. F., Natsoulis, G., and Boeke, J. D. (1993). Hotspots for unselected Ty1 transposition events on yeast chromosome III are near tRNA genes and LTR sequences. Cell 73, 1007–1018.

Kalpana, G. V., and Goff, S. P. (1993). Genetic analysis of homomeric interactions of human immunodeficiency virus type 1 integrase using the yeast two-hybrid system. Proc. Natl. Acad. Sci. USA 90, 10593–10597.

Katz, R. A., Merkel, G., Kulkovsky, J., Leis, J., and Skalka, A. M. (1990). The avian retroviral IN protein is both necessary and sufficient for integrative recombination in vitro. Cell 63, 87–95.

Khavari, P. A., Peterson, C. L., Tamkun, J. W., Mendel, D. B., and Crabtree, G. R. (1993). BRG1 contains a conserved domain of the SWI2/SNF2 family necessary for normal mitotic growth and transcription. Nature 366, 170–174.

King, W., Patel, M., Lobel, L. I., Goff, S. P., and Nguyen-Huu, C. (1985). Insertion mutagenesis of embryonal carcinoma cells by retrovirus infection. Science 228, 554–558.

Kozak, M. (1991). Structural features in eukaryotic mRNAs that modulate the initiation of translation. J. Biol. Chem. 266, 19867–19870.

Kruger, W., and Herskowitz, I. (1991). A negative regulator of HO transcription, SIN1 (SPT2), is a nonspecific DNA-binding protein related to HMG1. Mol. Cell. Biol. 11, 4135–4146.

Laurent, B., and Carlson, M. (1992). Yeast SNF2/SWI2, SNF5, and SNF6 proteins function coordinately with the gene-specific transcriptional activators GAL4 and Bicoid. Genes Dev. 6, 1707–1715.

Laurent, B. C., Treich, I., and Carlson, M. (1993). The yeast SNF2/SWI2 protein has DNA-stimulated ATPase activity required for transcriptional activation. Genes Dev. 7, 583–591.

Laurent, B. C., Treitel, M. A., and Carlson, M. (1990). The SNF5 protein of Saccharomyces cerevisiae is a glutamine- and proline-rich transcriptional activator that affects expression of a broad spectrum of genes. Mol. Cell. Biol. 10, 5616–5625.

Laurent, B. C., Treitel, M. A., and Carlson, M. (1991). Functional interdependence of the yeast SNF2, SNF5, and SNF6 proteins in transcriptional activation. Proc. Natl. Acad. Sci. USA 88, 2687–2691.

Laurent, B. C., Yang, X., and Carlson, M. (1992). An essential Saccharomyces cerevisiae gene homologous to SNF2 encodes a helicase-related protein in a new family. Mol. Cell. Biol. 12, 1893–1902.

Luban, J., Alin, K. B., Bossolt, K. L., Humaran, T., and Goff, S. P. (1992). Genetic assay for multimerization of retroviral gag polyproteins. J. Virol., 66, 5157–5160.

Luban, J., Bossolt, K. L., Franke, E. K., Kalpana, G. V., and Goff, S. P. (1993). Human immunodeficiency virus type 1 gag protein binds to cyclophilins A and B. Cell 73, 1067–1078.

Maniatis, T., Fristch, E. F., and Sambrook, J. (1982). Molecular cloning, a laboratory manual. (Cold Spring Harbor, N.Y.: Cold Spring Harbor).

Muchardt, C., and Yaniv, M. (1993). A human homologue of Saccharomyces cerevisiae SNF2/SWI2 and Drosophila brm genes potentiates transcriptional activation by the glucocorticoid receptor. EMBO J. 12, 4279–4290.

Natsoulis, G., Thomas, W., Roghmann, M.-C., Winston, F., and Boeke, J. D. (1989). Ty1 transposition in Saccharomyces cerevisiae is nonrandom. Genetics 123, 269–279.

Neigeborn, L., and Carlson, M. (1984). Genes affecting the regulation of SUC2 gene expression by glucose repression in Saccharomyces Cerevisiae. Genetics 108, 845–858.

Okabe, I., Bailey, L., Attree, O., Srinivasan, S., Perkel, J., Laurent, B., Carlson, M., Nelson, D., and Nussbaum, R. (1992). Cloning of human and bovine homologs of SNF2/SWI2: a global activator of transcription in yeast S. cerevisiae. Nucleic Acids Research 20, 4649–4655.

Peterson, C. L., and Herskowitz, I. (1992). Characterization of the yeast SWI1, SWI2, and SWI3 genes, which encode a global activator of transcription. Cell 68, 573–583.

Pryciak, P. M., Sil, A., and Varmus, H. A. (1991). Retroviral integration into minichromosomes in vitro. EMBO J. 11, 769–780.

Rohdewohld, H., Weiher, H., Reik, W. Jaenisch, R., and Breindl, M. (1987). Retrovirus integration and chromatin structure: Moloney murine leukemia proviral integration sites map near DNAse I-hypertensive sites. J. Virol. 61, 336–343.

Sandmeyer, S. B., Hansen, L. J., and Chalker, D. L. (1990). Integration specificity of retrotransposons and retroviruses. Ann. Rev. Genet. 24, 491–518.

Scherdin, U., Rhodes, K., and Breidl, M. (1990). Transcriptionally active genome regions are preferred targets for retrovirus integration. J. Virol. 64, 907–912.

Schwartzberg, P., Colicelli, J., and Goff, S. P. (1984). Construction and analysis of deletion mutations in the pol gene of Moloney murine leukemia virus: a new viral function required for productive infection. Cell 37, 1043–1052.

Shih, C.-C., Stoye, J. P., and Coffin, J. M. (1988). Highly preferred targets for retroviral integration. Cell 53, 531–537.

Shimotohno, K., and Temin, H. M. (1980). No apparent nucleotide sequence specificity in cellular DNA juxtaposed to retrovirus proviruses. Proc. Natl. Acad. Sci. USA 77, 7357–7361.

Shoemaker, C., Hoffman, J., Goff, S., and Baltimore, D. (1981). Intramolecular integration within Moloney murine leukemia virus DNA. J. Virol. 40, 164–172.

Varmus, H. E., Quintrell, N., and Ortiz, S. (1981). Retroviruses as mutagens: insertions and excision of a nontransforming provirus after expression of a resident transforming provirus. Cell 25, 23–36.

Vijaya, S., Steffen, D. L., and Robinson, H. L. (1986). Acceptor sites for retroviral integrations map near DNAse I-hypertensive sites in chromatin. J. Virol. 60, 683–692.

Weiss, R., Teich, N., Varmus, H., and Coffin, J. (1984). RNA tumor viruses. (Cold Spring Harbor, N.Y.: Cold Spring Harbor).

Winston, F., and Carlson, M. (1992). Yeast SNF/SWI transcriptional activators and the SPT/SIN chromatin connection. Topics in Genet. 8, 387–391.

Yoshinaga, S. K., Peterson, C. L., Herskowitz, I., and Yammamoto, K. R. (1992). Roles of SWI1, SWI2, and SWI3 proteins for transcriptional enhancement by steroid receptors. Science 258, 1598–1604.

What is claimed is:

1. An isolated nucleic acid encoding for a protein capable of interacting with the HIV-1 integrase, designated Ini-1, having the nucleotide sequence set forth in SEQ ID NO.: 1.

2. The isolated nucleic acid of claim 1 wherein said nucleic acid is labeled with a detectable moiety selected from the group consisting of a fluorescent label, radioactive label, and chemiluminescent label.

3. The isolated nucleic acid of claim 1 wherein said nucleic acid is DNA.

4. The isolated nucleic acid of claim 1 wherein said nucleic acid is cDNA.

5. The isolated nucleic acid of claim 3 wherein said nucleic acid is labeled with a detectable moiety selected from the group consisting of a fluorescent label, radioactive label, and chemiluminescent label.

6. A vector comprising the nucleic acid of claim 1.

7. The vector of claim 6 wherein the nucleic acid is cDNA.

8. The vector of claim 6 wherein said vector is a plasmid.

9. The vector of claim 7 wherein said vector is a plasmid.

10. A host cell containing the vector of claim 6.

11. A host cell containing the vector of claim 7.

12. The host cell of claim 10 wherein said host cell is a eukaryotic cell.

13. The host cell of claim 10 wherein said host cell is a prokaryotic cell.

14. The host cell of claim 11 wherein said host cell is a eukaryotic cell.

15. The host cell of claim 11 wherein said host cell is a prokaryotic cell.

\* \* \* \* \*